(12) United States Patent
Foo et al.

(10) Patent No.: US 11,294,016 B1
(45) Date of Patent: Apr. 5, 2022

(54) SYSTEM AND METHOD FOR CALIBRATION OF ASYMMETRIC GRADIENT CONCOMITANT FIELD CORRECTION PARAMETERS

(71) Applicant: GE Precision Healthcare LLC, Wauwatosa, WI (US)

(72) Inventors: Thomas K. F. Foo, Clifton Park, NY (US); Louis M. Frigo, Brookfield, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 0 days.

(21) Appl. No.: 17/111,480

(22) Filed: Dec. 3, 2020

(51) Int. Cl.
*G01R 33/565* (2006.01)
*A61B 5/055* (2006.01)

(52) U.S. Cl.
CPC ........ *G01R 33/56581* (2013.01); *A61B 5/055* (2013.01); *G01R 33/56554* (2013.01)

(58) Field of Classification Search
CPC ........ G01R 33/56581; G01R 33/56554; A61B 5/055
See application file for complete search history.

(56) References Cited

U.S. PATENT DOCUMENTS

| | | | |
|---|---|---|---|
| 6,064,205 A | 5/2000 | Zhou | |
| 6,515,478 B1 | 2/2003 | Wicklow | |
| 9,911,062 B1* | 3/2018 | Ahmad | G01R 33/56383 |
| 2009/0253983 A1* | 10/2009 | Foo | G01R 33/563 600/420 |
| 2009/0256568 A1* | 10/2009 | Wiesinger | G01R 33/56316 324/312 |
| 2018/0203088 A1 | 7/2018 | Tao | |
| 2020/0300947 A1* | 9/2020 | Wang | G01R 33/5616 |

OTHER PUBLICATIONS

Bernstein et al., "Concomitant gradient terms in phase contrast MR: analysis and correction," Magn Reson Med. Feb. 1998;39(2):300-8, 9 pages.
Bernstein et al., "Minimizing TE in moment-nulled or flow-encoded two- and three-dimensional gradient-echo imaging," J Magn Reson Imaging. Sep.-Oct. 1992;2(5):583-8, 6 pages.
Du et al., "Correction of concomitant magnetic field-induced image artifacts in nonaxial echo-planar imaging," Magn Reson Med. Sep. 2002;48(3):509-15, 7 pages.
Foo et al., "Highly efficient head-only magnetic field insert gradient coil for achieving simultaneous high gradient amplitude and slew rate at 3.0T (MAGNUS) for brain microstructure imaging," Magn Reson Med. Jun. 2020;83(6):2356-2369, 20 pages.

(Continued)

*Primary Examiner* — Dixomara Vargas

(57) ABSTRACT

A method for correcting concomitant gradient field effects in a magnetic resonance imaging (MRI) system includes determining a plurality of first phase difference measurements between two acquisitions using a plurality of first bipolar gradient waveforms applied to a first gradient coil. A first gradient coil constant is determined based on the plurality of first phase difference measurements and compensatory gradient waveforms are determined based on the first gradient coil constant. The compensatory gradient waveforms are applied to the gradient coils along with target gradient waveforms to compensate for a concomitant gradient field.

20 Claims, 14 Drawing Sheets

(56) References Cited

OTHER PUBLICATIONS

Foo et al., "Lightweight, compact, and high-performance 3T MR system for imaging the brain and extremities," Magn Reson Med. Nov. 2018;80(5):2232-2245. doi: 10.1002/mrm.27175. Epub Mar. 13, 2018, 24 pages.
Jones et al., "Microstructural imaging of the human brain with a 'super-scanner': 10 key advantages of ultra-strong gradients for diffusion MRI," Neuroimage. Nov. 15, 2018;182:8-38, 31 pages.
King et al., "Concomitant gradient field effects in spiral scans," Magn Reson Med. Jan. 1999;41(1):103-12, 10 pages.
Lee et al., "Peripheral nerve stimulation characteristics of an asymmetric head-only gradient coil compatible with a high-channel-count receiver array." Magn Reson Med. Dec. 2016;76(6):1939-1950, 25 pages.
Mathieu et al., "Design of high performance gradient coil for 3T head specialty scanner," Proceedings of 20th Annual Meeting ISMRM (Proceedings of ISMRM, 2012), p. 2588, 1 page.
Meier et al., "Concomitant field terms for asymmetric gradient coils: consequences for diffusion, flow, and echo-planar imaging," Magn Reson Med. Jul. 2008;60(1):128-34, 7 pages.
Norris et al., "Concomitant magnetic field gradients and their effects on imaging at low magnetic field strengths," Magn Reson Imaging. 1990;8(1):33-7, 5 pages.
Setsompop et al., "Blipped-controlled aliasing in parallel imaging for simultaneous multislice echo planar imaging with reduced g-factor penalty," Magn Reson Med. May 2012;67(5):1210-24, 28 pages.
Setsompop et al., "Pushing the limits of in vivo diffusion MRI for the Human Connectome Project," Neuroimage; Oct. 15, 2013; 80:220-33, 33 pages.
Tan et al., "Peripheral nerve stimulation limits of a high amplitude and slew rate magnetic field gradient coil for neuroimaging," Magn Reson Med 2020; 83: 352-366, 36 pages.
Tao et al., "Gradient pre-emphasis to counteract first-order concomitant fields on asymmetric MRI gradient systems," Magn Reson Med. Jun. 2017;77(6):2250-2262, 27 pages.
Weavers et al., "B0 concomitant field compensation for MRI systems employing asymmetric transverse gradient coils," Magnetic resonance in medicine, (2018), 79(3), 1538-1544, 15 pages.
Zhou et al., "Artifacts induced by concomitant magnetic field in fast spin-echo imaging," Magn Reson Med. Oct. 1998;40(4):582-91, 10 pages.
Zhou et al., "Correction of Concomitant magnetic-field-induced artifacts in axial echo planar imaging," Magn Reson Med. Apr. 1998;39(4), 1 page.

* cited by examiner

SYSTEM AND METHOD FOR CALIBRATION OF ASYMMETRIC GRADIENT CONCOMITANT FIELD CORRECTION PARAMETERS

This invention was made with Government support under contract W81XWH-16-2-0054 awarded by the Department of Defense. The Government has certain rights in the invention.

BACKGROUND

The field of the disclosure relates generally to systems and methods of magnetic resonance imaging (MRI), and more particularly, to systems and methods of calibrating asymmetric gradient concomitant field correction parameters in MRI.

MRI has proven useful in diagnosis of many diseases. MRI provides detailed images of soft tissues, abnormal tissues such as tumors, and other structures, which cannot be readily imaged by other imaging modalities, such as computed tomography (CT). Further, MRI operates without exposing patients to ionizing radiation experienced in modalities such as CT and x-rays.

In a MRI system, a large magnet produces a very strong magnetic field over the patient's body. The magnetic field produced by the large magnet is quite uniform or homogeneous. Gradient coils in the MRI system produce gradients which distorts this uniform magnetic field. In general, the gradients cause the change in field strength of the magnetic field in the patient body from one point to another.

In some MRI systems, high gradient amplitude coils are used to achieve higher image quality or when good spatial resolution is required. High gradient amplitude coils are capable of producing up to 400 mT/m magnetic gradient fields and/or may have coil efficiencies of $\eta=0.13$-$0.32$ mT/m/A. This compares with coil efficiencies of conventional gradient coils of $\eta=0.08$-$0.10$ mT/m/A. Examples of such gradient coils are the Connectome gradients with a maximum gradient amplitude ($G_{max}$) of 300 mT/m, the Compact 3T MRI system with $G_{max}=80$ mT/m, and the MAGNUS (microstructure anatomy gradient for neuroimaging with ultrasfast scanning) gradient system with $G_{max}=200$-$400$ mT/m, depending on the gradient driver maximum current output. Of these, the Compact 3T and MAGNUS gradient coils are smaller head-sized asymmetric gradient coils. As such, the maximum gradient fields that are generated by high gradient coils are far in excess of conventional gradients coils. This presents formidable systems engineering issues as the gradient coils and the associated gradient field corrections depend on accurate and proper calibration of gradient coil parameters. The gradient field corrections are necessary to compensate for non-linearity in the gradient field strength which gets worse farther from isocenter of the magnetic field.

Therefore, there is a need for an improved magnetic resonance imaging system and method.

BRIEF DESCRIPTION

In accordance with an embodiment of the present technique, a method for correcting concomitant gradient effects in a magnetic resonance imaging (MRI) system is presented. The method includes determining a plurality of first phase difference measurements between two acquisitions using a plurality of first bipolar gradient waveforms applied to a first gradient coil axis or direction. A first gradient coil axis' constant is determined based on the plurality of first phase different measurements. With the determined first gradient coil (axis) constant, compensatory gradient waveforms related to that gradient coil axis are determined. Finally, the compensatory gradient waveforms are applied along with target gradient waveforms to compensate for a concomitant gradient field. The compensatory waveforms may be applied on other gradient axes in addition to the first gradient coil axis.

In accordance with another embodiment of the present technique, a method for correcting concomitant gradient effects in an MRI system is presented. The method includes determining a plurality of first phase difference measurements between two acquisitions using a plurality of first bipolar gradient waveforms applied to a first gradient coil (axis). The method further includes determining a plurality of second phase difference measurements between two acquisitions using a plurality of second bipolar gradient waveforms applied to a second gradient coil (axis). First and second gradient coil constants are determined based on the plurality of first phase difference measurements and the plurality of second phase difference measurements respectively. The method also includes determining compensatory gradient waveforms based on the first and second gradient coil constants and applying the compensatory gradient waveforms with target gradient waveforms to compensate for a concomitant gradient field.

In accordance with yet another embodiment of the present technique, a MRI system is presented. The MRI system includes a magnet configured to generate a polarizing magnetic field about at least a portion of a subject arranged in the MRI system and a gradient coil assembly including a plurality of gradient coils configured to apply at least one gradient field to the polarizing magnetic field. The MRI system further includes a radio frequency (RF) system configured to apply an RF field to the subject and to receive magnetic resonance signals from the subject and a processing system. The processing system is programmed to determine a plurality of phase difference measurements between two acquisitions using a plurality of bipolar gradient waveforms applied to at least one gradient coil of the plurality of gradient coils. The processing system is also programmed to determine at least one gradient coil constant based on the plurality of phase difference measurements and to determine compensatory gradient waveforms based on the at least one gradient coil constant. The processing system is further programmed to apply the compensatory gradient waveforms to the plurality of gradient coils to compensate for a concomitant gradient field.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
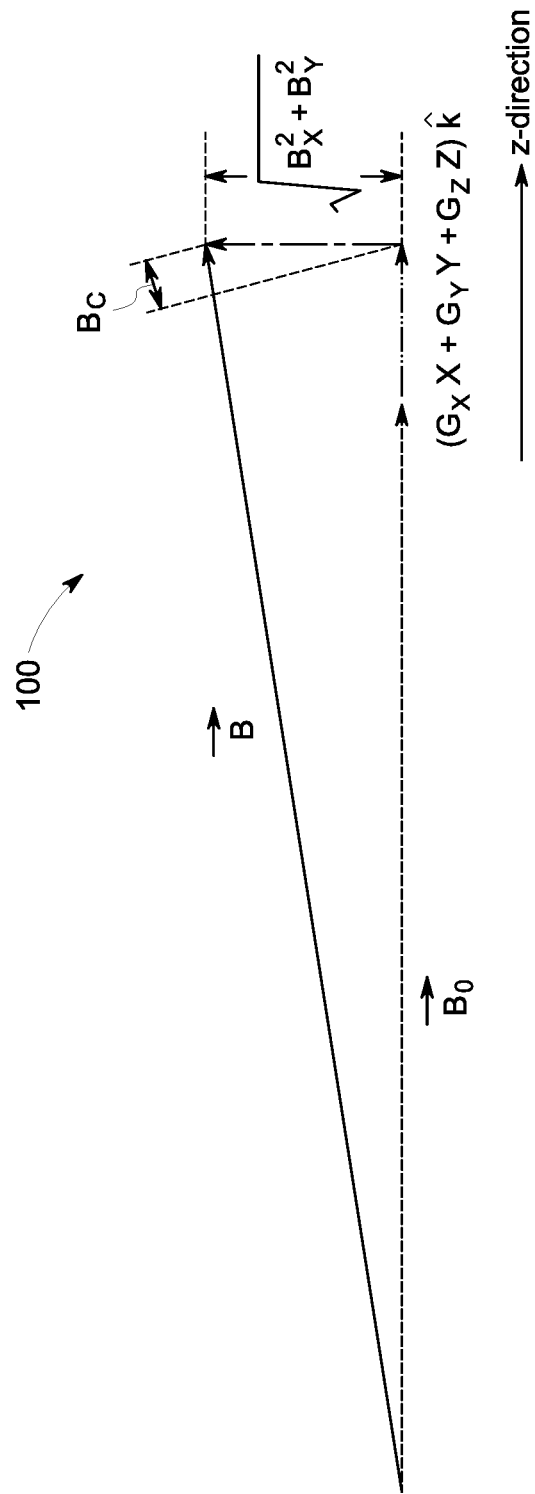
FIG. 1 is a vector diagram of calculation of the concomitant gradient field, in accordance with aspects of the present approach.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present embodiments, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments. Furthermore, the terms "circuit" and "circuitry" and "controller" may include either a single component or a plurality of components, which are either active and/or passive and are connected or otherwise coupled together to provide the described function.

In magnetic resonance imaging (MRI), an object is placed in a magnet. When the object is in the magnetic field generated by the magnet, magnetic moments of nuclei, such as protons, attempt to align with the magnetic field but process about the magnetic field in a random order at the nuclei's Larmor frequency. The magnetic field of the magnet is referred to as B0 and extends in the longitudinal or z direction. In acquiring a MR image, a magnetic field (referred to as an excitation field B1), which is in the x-y plane and near the Larmor frequency, is generated by a radio-frequency (RF) coil and may be used to rotate, or "tip," the net magnetic moment $M_z$ of the nuclei from the z direction to the transverse or x-y plane. A signal, which is referred to as a MR signal, is emitted by the nuclei, after the excitation signal B1 is terminated. To use the MR signals to generate an image of an object, magnetic field gradient pulses ($G_x$, $G_y$, and $G_z$) are used. The gradient pulses are used to scan through the k space, the space of spatial frequencies or inverse of distances. A Fourier relationship exists between the acquired MR signals and an image of the object, and therefore the image of the object can be derived by reconstructing the MR signals.

In MRI, when higher amplitude applied gradient fields are applied, the effects of concomitant gradient fields become more significant. Concomitant fields are the result of applied linear gradient fields, nominally only in the z-direction or in the direction of the main static magnetic field, having non-linear spatially varying additional fields in the x or y directions. These concomitant fields are a direct consequence of the need to satisfy Maxwell's equations which establish that there can be no magnetic monopoles $\nabla \cdot \vec{B}=0$ or current sources in the field $\nabla \times \vec{B}=0$. As a result of applying a pure linear x or y or z gradients (i.e., $G_x x\hat{i}$, $G_y y\hat{j}$, or $G_z z\hat{k}$ fields) along the z-direction, off-axis gradient fields are established, where $\hat{i}, \hat{j}, \hat{k}$ are unit vectors in the x, y, and z directions, respectively. For example, applying a pure linear x gradient field, $G_x$, for symmetric gradient coils, results in $$\vec{B}=G_x z\hat{i}+(B_0+G_x x)\hat{k} \quad (1)$$

that is, an additional field that is spatially varying in the z-direction, and where $B_0\hat{k}$ is the main static magnetic field. Similarly, for a pure linear z gradient field, $G_z$, results in $$\vec{B}=-\alpha G_z x\hat{i}+(\alpha-1)G_z y\hat{j}+(B_0+G_z z)\hat{k} \quad (2)$$

where $\alpha$ is a symmetry parameter and describes the strength of the resulting field along the x- and y-axes to the applied $G_z$ gradient field. For the typical MRI gradient coils where there is cylindrical symmetry, $\alpha=0.5$. In short, the consequence of satisfying Maxwell's equations is that an additional concomitant field that distorts the primary applied field is established. This additional field generates non-linear spatially varying fields that contribute to phase errors or spatial offsets in a host of MRI applications from echo planar imaging (EPI) to phase contrast flow-imaging and quantitative diffusion.

FIG. 1 illustrates a vector diagram 100 of calculation of the additional concomitant gradient field. The vector diagram 100 shows a main magnetic field vector $B_0$ in z direction. Vector diagram 100 further shows a desired gradient field vector, $(G_x x+G_y y+G_z z)\hat{k}$ in z direction, which is a result of, applying a pure linear x or y or z gradient fields along the z-direction. As described earlier, the application of pure linear gradient field establishes off-axis gradient fields shown by a vector, concomitant field $B_c$, in vector diagram 100. Further, as shown in vector diagram 100, the amplitude of the concomitant field vector $B_c$ is $\sqrt{B_x^2+B_y^2}$, i.e., the magnitude of the off-z-axis magnetic fields. The addition of concomitant field vector $B_e$, and main magnetic field vector $B_0$ and the desired gradient field vector $(G_x x + G_y y + G_z z)\hat{k}$ results in a total magnetic field vector $\vec{B}$. As a result, the amplitude of the total magnetic field vector $\vec{B}$ is greater than the desired magnetic field amplitude i.e., $|\vec{B}| > (B_0 + G_x x + G_y y + G_z z)$.

It should be noted that the additional concomitant gradient field is generated for both symmetric, as well as for asymmetric gradient coils. In a symmetric coil, the magnetic and physical isocenters are both configured to be disposed in a common plane e.g., patient's eyes or patient's heart. On the other hand, asymmetric gradient coils are asymmetric relative to z-direction and therefore, their magnetic and physical isocenters are not disposed in a common plane. Asymmetric gradient coil designs have been noted to produce additional zeroth and first order concomitant gradient fields compared to symmetric gradient coils, which have substantial second order terms. The invention described herein pertains to calibration of asymmetric gradient coils post-installation as the correction factors are dependent on parameters that are unique to the gradient coil installation. In particular, the invention described allows for calibration of correction factors to ensure that the correct concomitant gradient factors are applied. These parameters may change from system-to-system as the insertion position of the gradient coil may vary. As such, a fast and accurate method to determine these offsets is important.

Figure 2:
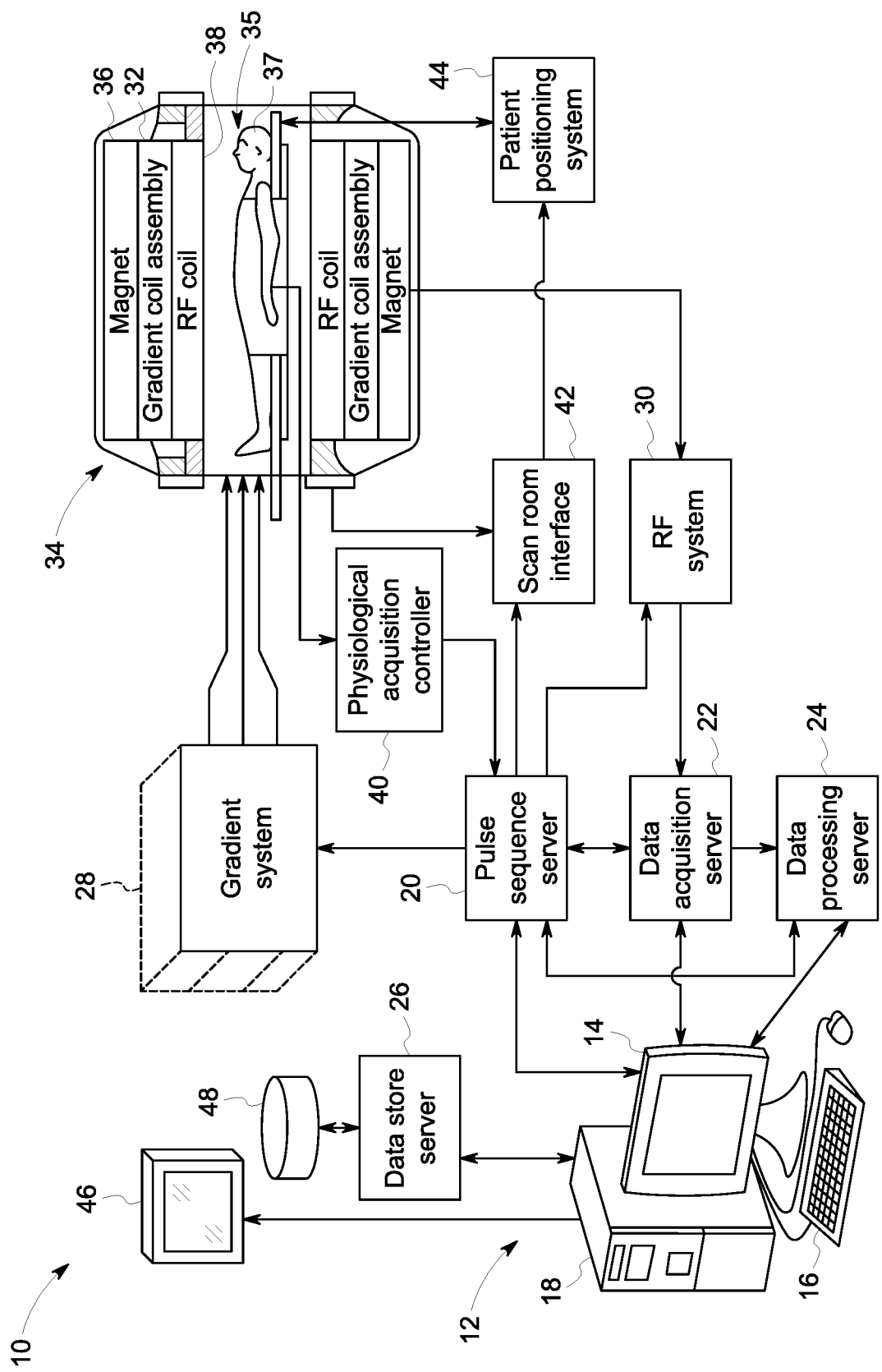
FIG. 2 is a schematic diagram of an exemplary MRI system, in accordance with aspects of the present approach.

FIG. 2 illustrates a schematic diagram of an exemplary MRI system 10. In the exemplary embodiment, the MRI system 10 includes a workstation 12 having a display 14 and a keyboard 16. The workstation 12 includes a processor 18, such as a commercially available programmable machine running a commercially available operating system. The workstation 12 provides an operator interface that allows scan prescriptions to be entered into the MRI system 10. The workstation 12 is coupled to a pulse sequence server 20, a data acquisition server 22, a data processing server 24, and a data store server 26. The workstation 12 and each server 20, 22, 24, and 26 communicate with each other and together may be called as a processing system.

In the exemplary embodiment, the pulse sequence server 20 responds to instructions downloaded from the workstation 12 to operate a gradient system 28 and a radiofrequency ("RF") system 30. The instructions are used to produce gradient and RF waveforms in MR pulse sequences. An RF coil 38 and a gradient coil assembly 32 are used to perform the prescribed MR pulse sequence. The RF coil 38 is shown as a whole-body RF coil. The RF coil 38 may also be a local coil that may be placed in proximity to the anatomy to be imaged, or a coil array that includes a plurality of coils.

In the exemplary embodiment, gradient waveforms used to perform the prescribed scan are produced and applied to the gradient system 28, which includes gradient amplifiers and excites gradient coils in the gradient coil assembly 32 to produce the magnetic field gradients $G_x$, $G_y$, and $G_z$ used for position-encoding MR signals. The gradient coil assembly 32 forms part of a magnet assembly 34 that also includes a polarizing magnet 36 and the RF coil 38. The magnet assembly 34 forms a bore 35, where an object 37 such as a patient is received and scanned. The magnet 36 produces a polarizing magnetic field around the patient and the gradient coil assembly 32 applies the magnetic gradient field to the polarizing magnetic field. Further, In the exemplary embodiment, the RF system 30 includes an RF transmitter for producing RF pulses used in MR pulse sequences. The RF transmitter is responsive to the scan prescription and direction from the pulse sequence server 20 to produce RF pulses of a desired frequency, phase, and pulse amplitude waveform. The generated RF pulses may be applied to the RF coil 38 by the RF system 30 which applies a RF field to the patient. Responsive MR signals detected by the RF coil 38 are received by the RF system 30, amplified, demodulated, filtered, and digitized under direction of commands produced by the pulse sequence server 20. The RF coil 38 is described as a transmitter and receiver coil such that the RF coil 38 transmits RF pulses and detects MR signals. In one embodiment, the MRI system 10 may include a transmitter RF coil that transmits RF pulses and a separate receiver coil that detects MR signals. A transmission channel of the RF system 30 may be connected to a RF transmission coil and a receiver channel may be connected to a separate RF receiver coil. Often, the transmission channel is connected to the whole-body RF coil 38 and each receiver section is connected to a separate local RF coil.

In the exemplary embodiment, the RF system 30 also includes one or more RF receiver channels. Each RF receiver channel includes an RF amplifier that amplifies the MR signal received by the RF coil 38 to which the channel is connected, and a detector that detects and digitizes the I and Q quadrature components of the received MR signal. The magnitude M of the received MR signal may then be determined as the square root of the sum of the squares of the I and Q components as in Eq. (3) below:

$$M = \sqrt{I^2 + Q^2} \tag{3}$$

and the phase $\phi$ of the received MR signal may also be determined as in eq. (4) below:

$$\phi = \tan^{-1}\left(\frac{Q}{I}\right) \tag{4}$$

In the exemplary embodiment, the digitized MR signal samples produced by the RF system 30 are received by the data acquisition server 22. The data acquisition server 22 may operate in response to instructions downloaded from the workstation 12 to receive real-time MR data and provide buffer storage such that no data is lost by data overrun. In some scans, the data acquisition server 22 does little more than pass the acquired MR data to the data processing server 24. In scans that need information derived from acquired MR data to control further performance of the scan, however, the data acquisition server 22 is programmed to produce the needed information and convey it to the pulse sequence server 20. For example, during prescans, MR data is acquired and used to calibrate the pulse sequence performed by the pulse sequence server 20. Also, navigator signals may be acquired during a scan and used to adjust the operating parameters of the RF system 30 or the gradient system 28, or to control the view order in which k space is sampled.

In the exemplary embodiment, the data processing server 24 receives MR data from the data acquisition server 22 and processes it in accordance with instructions downloaded from the workstation 12. Such processing may include, for example, Fourier transformation of raw k-space MR data to produce two or three-dimensional images, the application of filters to a reconstructed image, the performance of a back-projection image reconstruction of acquired MR data, the generation of functional MR images, and the calculation of motion or flow images.

With the preceding discussion of an MRI system 10 in mind, we can go back to the concomitant field discussion. As discussed earlier, the application of the linear gradient field in z direction results in generation of a concomitant fields i.e., non-linear spatially varying additional fields in the x or y directions. The invention described herein pertains to calibration of asymmetric gradient coils which is useful in compensating for the concomitant fields.

The application of a high amplitude gradient field, $G_z\hat{k}$, directed along the direction of the main static magnetic field, $\vec{B}_0$ results in a spatially-varying modification of the main magnetic field, where the desired magnetic field $$\vec{B}_{desired} = (B_0 + (G_x x + G_y y + G_z z))\hat{k} \quad (5)$$

results in a total magnetic field vector of:

$$\vec{B} = (G_x(z+z_{0x}) - \alpha G_z(x+x_0))\hat{i} + (G_y(z+z_{0y}) - (1-\alpha) G_z(y+y_0))\hat{j} + (B_0 + G_x x + G_y y + G_z z)\hat{k} \quad (6)$$

which leads to non-zero components of the field in the x or y directions. In the above equation, the first component associated with $\hat{i}$ is $B_x$, second component associated with $\hat{j}$ is $B_y$, and third component associated with $\hat{k}$ is $B_z$. Further, $G_x$, $G_y$, and $G_z$ are the applied gradient fields that are spatially varying along the x, y, and z directions, respectively. $x_0$, $y_0$, $z_{0x}$ and $z_{0y}$ are the offsets of the gradient field components relative to the magnet isocenter. Specifically, $x_0$ and $y_0$ are the offsets of the z-gradient coil in the x and y directions, respectively, and $z_{0x}$ and $z_{0y}$ are the offsets of the transverse (x and y gradient coils) in the z-direction, respectively. In general, for symmetric gradient coils, $x_0 = y_0 = z_{0x} = z_{0y} = 0$ as they are coincident with the magnet isocenter.

For asymmetric gradient coils, $z_{0x} \neq 0$ and $z_{0y} \neq 0$. Furthermore, it is possible that $z_{0x} \neq z_{0y}$, that is, the offsets in the transverse gradients may not be necessarily be identical. However, in most cases, $z_{0x} = z_{0y}$. The technique described herein allows a determination of whether $z_{0x} = z_{0y}$ or not, and if not, the individual values of $z_{0x}$ and $z_{0y}$ (for $z_{0x} \neq z_{0y}$). Although $z_{0x}$ and $z_{0y}$ are typically determined from the design stage of the gradient coils (i.e., default values), manufacturing tolerances and gradient coil assembly and installation may result is a departure of $z_{0x}$ and $z_{0y}$ from the expected or values from the design. In the ensuing discussion, the z-gradient coil (but not x or y gradient coil) is assumed to be symmetric. There are practical reasons why the z-gradient coil is symmetric as it is desirable that the offsets of the asymmetric coil from isocenter be as closely aligned as possible. In other words, although it is possible to have a fully asymmetric gradient coil on for all three axes (x, y and z), typically, only the transverse axes (x and y) are asymmetrical as there is difficulty in aligning the transverse axes gradient coils with the z gradient coil to avoid significant eddy currents, and to facilitate adequate force- and torque-balancing. As such, for symmetric z gradient coil, $x_0 = y_0$. The invention described herein pertains then to calibration of $z_{0x}$ and $z_{0y}$, which are gradient coil constants specific to the transverse gradient axes and are useful in correcting the gradient coils waveforms to compensate for the concomitant magnetic field.

As shown in FIG. 1 and in Eqn. (6), the magnitude of the total magnetic field can be written as:

$$|\vec{B}| \approx B_z + B_c = \sqrt{B_x^2 + B_y^2 + B_z^2} \quad (7)$$

where $B_x$, $B_y$, and $B_z$ are the x, y, and z direction components of $\vec{B}$ respectively. As the desired field is $B_z$, using the Taylor series expansion, $$(1+u)^{\frac{1}{2}} \simeq 1 + \frac{1}{2}u - \frac{1}{8}u^2 + \frac{1}{16}u^3 + \ldots \quad (8)$$

Eqn. (7) can be solved by using substitution, $$u = \frac{B_x^2 + B_y^2}{B_z^2}.$$

As such, $$|\vec{B}| = B_z\left(1 + \frac{B_x^2 + B_y^2}{B_z^2}\right)^{\frac{1}{2}} \quad (9)$$

$$= B_z + \frac{B_x^2 + B_y^2}{2B_z} - \frac{(B_x^2 + B_y^2)^2}{8B_z^3} + \frac{(B_x^2 + B_y^2)^3}{16B_z^5} + \ldots$$

where $B_x$, $B_y$, and $B_z$ are given in Eqn. (6). The concomitant field that is in addition to the desired field, from Eqn. (7), is then $B_c = |\vec{B}| - B_z$, where $$B_c = \frac{B_x^2 + B_y^2}{2B_z} - \frac{(B_x^2 + B_y^2)^2}{8B_z^3} + \frac{(B_x^2 + B_y^2)^3}{16B_z^5} + \ldots \quad (10)$$

from which the zeroth ($0^{th}$), first ($1^{st}$), second ($2^{nd}$) and higher order concomitant gradient fields can be extracted. The order of the concomitant gradient fields represents the order of the spatial variation. That is, zeroth order concomitant field is independent of spatial location, first order varies linearly with spatial location, second order varies quadratically with spatial location, third order varies cubicly with spatial location, and similarly for the higher order concomitant fields.

With low-performance gradient coils, it can be assumed that the higher-ordered terms are negligible and corrections for only zeroth, first, and second order may be needed. However, with higher performance gradient coils, third order corrections may also be needed. High performance gradient coils are capable of producing up to 400 mT/m magnetic gradient fields and/or may have coil efficiencies of $\eta = 0.13 - 0.32$ mT/m/A. To quantify the significance of the higher ordered terms, Eqn. (10) can be expanded using the definitions of Eqn. (6) as $$|B_c| = \quad (11)$$

$$\frac{1}{2B_z}\left(G_x^2(z+z_{0x})^2 + \alpha^2 G_z^2(x+x_0)^2\right) - \frac{1}{B_z}(\alpha G_x G_z(z+z_{0x})(x+x_0)) +$$

$$\frac{1}{2B_z}\left(G_y^2(z+z_{0y})^2 + (1-\alpha)^2 G_z^2(y+y_0)^2\right) -$$

$$\frac{1}{B_z}((1-\alpha)G_y G_z(z+z_{0y})(y+y_0)) - \frac{1}{8B_z^3}[B_x^4 + B_y^4 + 2B_x^2 B_y^2]$$

where $$B_x^4 = G_x^4(z+z_{0x})^4 + \alpha^4 G_z^4(x+x_0)^4 - 6\alpha^2 G_x^2 G_z^2(z+z_{0x})^2 (x+x_0)^2 - 4\alpha G_x^3 G_z(z+z_{0x})^3(x+x_0) - 4\alpha^3 G_x G_z^3(x+x_0)^3(z+z_0) \quad (12)$$

$$B_y^4 = G_y^4(z+z_{0y})^4 + (1-\alpha)^4 G_z^4(y+y_0)^4 - 6(1-\alpha)^2 G_y^2 G_z^2 (z+z_{0y})^2(y+y_0)^2 - 4(1-\alpha)G_y^3 G_z(z+z_{0y})^3(y+y_0) - 4(1-\alpha^3)G_y G_z^3(z+z_{0y})(y+y_0)^3 \quad (13)$$

and $$B_x^2 B_y^2 = G_x^2 G_y^2 (z+z_{0x})^2 (z+z_{0y})^2 + (1-\alpha) G_x^2 G_z^2 (z+z_{0x})^2 (y+y_0)^2 - 2(1-\alpha) G_x^2 G_y G_z (z+z_{0x})(z+z_{0y})(y+y_0) + \alpha^2 G_y^2 G_z^2 (z+z_{0y})^2 (x+x_0) + \alpha^2 (1-\alpha)^2 G_z^4 (x+x_0)(y+y_0) - 2\alpha^2 (1-\alpha) G_y G_z^3 (z+z_{0y})(x+x_0)^2 (y+y_0) - 2\alpha G_x G_y^2 G_z (z+z_{0x})(z+z_{0y})^2 (x+x_0) - 2\alpha (1-\alpha) G_x G_z (z+z_{0x})(x+x_0)(y+y_0)^2 - 4\alpha(1-\alpha) G_x G_y G_z^2 (z+z_{0y})(x+x_0)(y+y_0) \quad (14)$$

Collecting terms from Eqn. (11) and using the definitions from Eqn. (12)-(14), we can define the zeroth, first, second, and third order spatial terms of the concomitant gradient. As such, the zeroth order term is $$|B_c|_{0th} = \frac{G_x^2 z_{0x}^2}{2B_z} + \frac{\alpha^2 G_x^2 x_0^2}{2B_z} - \frac{\alpha G_x G_z z_{0x} x_0}{B_z} + \frac{G_y^2 z_{0y}^2}{2B_z} + \frac{(1-\alpha)^2 G_z^2 y_0^2}{2B_z} - \frac{(1-\alpha) G_y G_z z_{0y} y_0}{B_z} \quad (15)$$

Since symmetric gradients (e.g., z-gradient coil) do not have zeroth and odd-ordered concomitant terms, asymmetric gradient coils (i.e., x and y) typically have only transverse x and y gradients that are asymmetric with the z gradient symmetric. Alignment of an asymmetric z gradient with an asymmetric transverse (x and y) gradients is difficult, it is preferred to have the z gradient be symmetric to simplify the force- and torque-balancing in the gradient design. Hence, for the high-performance head-gradient concomitant corrections (as an example), only asymmetric transverse gradients are considered. As such, we set $x_0 = y_0 = 0$, and $z_{0x} \neq 0$, $z_{0y} \neq 0$ in Eqn. (15), such that the zeroth order concomitant gradient field for asymmetric transverse and symmetric z gradients is:

$$|B_c|_{0th\_asym} = \frac{1}{2B_z}[G_x^2 z_{0x}^2 + G_y^2 z_{0y}^2] \quad (16)$$

with $\alpha = 0.5$. Assuming $B_z \approx B_0$, (as $B_0 >> (G_x x + G_y y + G_z z)$), the zeroth order error field is then $$B_{error,0th} \approx \frac{1}{2B_0}[G_x^2 z_{0x}^2 + G_y^2 z_{0y}^2] \quad (17)$$

Similarly, the first order concomitant field is $$|B_c|_{1st} = \frac{G_x^2 z z_{0x}}{B_z} + \frac{\alpha^2 G_x^2 x x_0}{B_z} - \frac{\alpha G_x G_z x z_{0x}}{B_z} - \frac{\alpha G_x G_z z x_0}{B_z} + \frac{G_y^2 z z_{0y}}{B_z} + \frac{(1-\alpha)^2 G_z^2 y y_0}{B_z} - \frac{(1-\alpha) G_y G_z y z_{0y}}{B_z} - \frac{(1-\alpha) G_y G_z z y_0}{B_z} \quad (18)$$

which simplifies in an asymmetric transverse gradient coil with a symmetric z gradient with $x_0 = y_0 = 0$ and $y_0 = 0$ and $\alpha = 0.5$ to $$|B_c|_{1st_{asym}} = \frac{G_x^2 z z_{0x}}{B_z} - \frac{G_x G_z x z_{0x}}{2B_z} + \frac{G_y^2 z z_{0y}}{B_z} - \frac{G_y G_z y z_{0y}}{2B_z} \quad (19)$$

$$B_{error,1st} \approx -\frac{G_x G_z z_{0x}}{2B_0} x - \frac{G_y G_z z_{0y}}{2B_0} y + \frac{(G_x^2 z_{0x} + G_y^2 z_{0y})}{B_0} z \quad (20)$$

Note that for symmetric transverse gradient coils (x and y axes), Eqn. (18) and Eqn. (20) disappear, i.e., there are no zeroth or first order concomitant fields for a fully symmetric gradient coil as $z_{0x} = z_{0y} = 0$.

The second order concomitant field is:

$$|B_c|_{2nd} = \frac{G_x^2 z^2}{2B_z} + \frac{\alpha^2 G_x^2 x^2}{B_z} - \frac{\alpha G_x G_z x z}{B_z} + \frac{G_y^2 z^2}{2B_z} + \frac{(1-\alpha)^2 G_z^2 y^2}{2B_z}$$
$$= \frac{\alpha^2 G_z^2}{2B_z} x^2 + \frac{(1-\alpha)^2 G_z^2}{2B_z} y^2 + \frac{(G_x^2 + G_y^2)}{2B_z} z^2 - \frac{\alpha G_x G_z}{B_z} xz - \frac{(1-\alpha) G_y G_z}{B_z} yz \quad (21)$$

and this approximates to $$B_{error,2nd} \approx \frac{G_z^2}{8B_0} x^2 + \frac{G_z^2}{8B_0} y^2 + \frac{(G_x^2 + G_y^2)}{2B_0} z^2 - \frac{G_x G_z}{2B_0} xz - \frac{G_y G_z}{2B_0} yz \quad (22)$$

which is common to and unchanged in both symmetric and as well as asymmetric gradient coils, where $\alpha = 0.5$.

The third-order spatial components in the Taylor series expansion in Eqn. (11) may be significant but the fourth-order spatial components can be ignored as the $-(z^3/2B_z^3)(G_x^4 z_{0x} + G_y^4 z_{0y})$ term is dominant. Hence, with $x_0 = y_0 = 0$, the third-order concomitant field for asymmetrical transverse gradients is $$|B_c|_{3rd\_asym} = -\frac{z^3}{2B_z^3}(G_x^4 z_{0x} + G_y^4 z_{0y} + G_x^2 G_z^2 z_{0x} + G_y^2 G_z^2 z_{0y}) + \frac{x^3}{2B_z^3}(\alpha^3 G_x G_z^3 z_{0x}) + \frac{y^3}{2B_z^3}((1-\alpha)^3 G_y G_z^3 z_{0y}) \quad (23)$$

-continued $$+\frac{xz^2}{2B_z^3}(3\alpha G_x^3 G_z z_{0x} + \alpha G_x G_y^2 G_z(z_{0x} + 2z_{0y}))$$

$$+\frac{x^2 z}{2B_z^3}(3\alpha^2 G_x^2 G_z^2 z_{0x} - \alpha^2 G_y^2 G_z^2 z_{0y})$$

$$+\frac{yz^2}{2B_z^3}(3(1-\alpha)G_y^3 G_z z_{0y} + (1-\alpha)G_x^2 G_y G_z(z_{0y} + 2z_{0x}))$$

$$+\frac{y^2 z}{2B_z^3}(3(1-\alpha)^2 G_y^2 G_z^2 z_{0y} - (1-\alpha)^2 G_x^2 G_y G_z z_{0x})$$

$$+\frac{x^2 y}{2B_z^3}(\alpha^2(1-\alpha)G_y G_z^3 z_{0y}) + \frac{xy^2}{2B_z^3}(\alpha(1-\alpha)^2 G_x G_z^3 z_{0x})$$

$$+\frac{xyz}{3B_z^3}(\alpha(1-\alpha)G_x G_y G_z^2(z_{0x} + z_{0y}))$$

If we ignore the x-z and y-z cross terms in Eqn. (23), the spatially varying third-order concomitant term that could contribute to a measurable phase in the MRI image can be approximated as a z direction, spatially varying error field $$B_{error,3rd} \approx -\frac{z^3}{2B_0^3}(G_x^4 z_{0x} + G_y^4 z_{0y} + G_x^2 G_y^2 z_{0x} + G_x^2 G_y^2 z_{0y}) \quad (24)$$

According to an embodiment of the present technique, after determining the first and second order concomitant field components, these components may be corrected in the MRI system by a correction field along z gradient which are generated by gradient pre-emphasis i.e., compensatory gradient waveforms. However, the third order concomitant field cannot be corrected by gradient pre-emphasis or a correction field along z but will need to be accounted for in post-processing. As can be observed from the above equations, to determine first, second and third order concomitant field components, first we need to determine the two parameters $z_{0x}$ and $z_{0y}$, which are gradient coil constants specific to the transverse gradient axes.

In accordance with an embodiment of the present technique, to determine the gradient coil constants, $z_{0x}$ and $z_{0y}$, a method based on a phase contrast MRI acquisition is utilized. A phase contrast MRI is a method that encodes for velocity of flowing spins in the body of a patient by using a two-acquisition scheme with a bipolar gradient reversing polarity between the two acquisitions of the flow encoding gradients. The phase difference between the two acquisitions is then taken. Stationary spins result in a zero phase whereas flowing spins will differentially accumulate a phase during the application of the bipolar gradients of different polarity. In the embodiment of the present technique, we image a stationary phantom. We expect a zero phase from a phase difference approach after applying the bipolar gradients. However, additional concomitant gradient fields yield a non-zero phase in the stationary phantom which can be measured and the gradient coil constants, $z_{0x}$ and $z_{0y}$, can then be determined.

Figure 3:
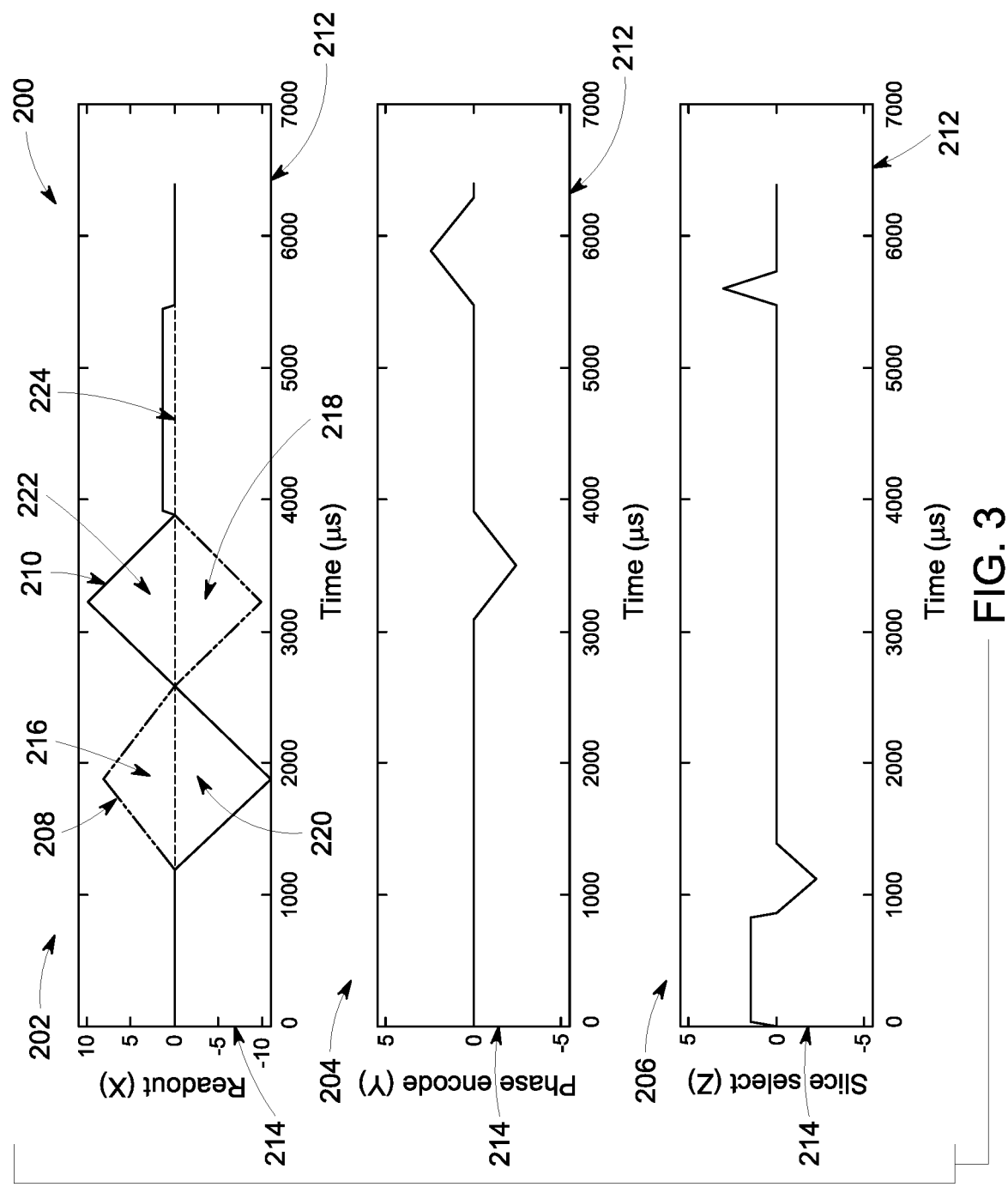
FIG. 3 is a graphical plot of typical bipolar phase contrast flow encoding imaging waveforms for a phase contrast MRI.

FIG. 3 shows a graphical plot 200 of phase contrast imaging waveforms for a phase contrast MRI. In FIG. 3, plot 202 shows a flow encoding gradient (X gradient), plot 204 shows a phase encoding gradient (Y gradient) and plot 206 shows a slice select gradient (Z gradient). In this example, a readout gradient 224 is also in the same direction as the flow encoding gradient (X gradient). A horizontal axis 212 and a vertical axis 214 in all plots 202, 204 and 206 show time in microseconds and gradient amplitude in Gauss/cm, respectively. The flow encoding gradient 202 is a bipolar gradient waveform that is toggled between a positive (+) polarity 208, and a negative (−) polarity 210. It can be seen from FIG. 3, that positive polarity gradient waveform 208 has two lobes i.e., triangular or trapezoidal pulse areas, a positive lobe 216 followed by a negative lobe 218. Further, negative polarity gradient waveform 210 also has two lobes, a negative lobe 220 followed by a positive lobe 222. It should be noted that positive lobe 222 is followed by the readout gradient pulse 224. However, for concomitant field calculation purpose, the gradient pulse 224 can be ignored as any phase contributions from this and other extraneous gradients (other than the bipolar gradients) are canceled out when taking the phase difference. For purposes of measuring the gradient coil constants, $z_{0x}$ and $z_{0y}$, we focus on the zeroth order concomitant gradient field effects. As such, after taking the phase difference, the resulting zeroth order concomitant gradient field from the other gradient waveforms that do not change and cancel out. The method described in this technique varies the amplitudes of the bipolar gradients and measures the resulting phase difference. By plotting the resulting phase difference as a function of the bipolar gradient amplitudes, the gradient coil constants, $z_{0x}$ and $z_{0y}$, can be determined.

Taking the phase difference between the two acquisitions 208 and 210 yield a net phase as the phase of static spins reverse with the polarity change. Considering the zeroth order concomitant gradient effect from Eqn. (17), it can be seen that the net effect of the concomitant gradient is positive irrespective of the gradient polarity given, the gradient amplitude term is squared in Eqn. (17). Further, the zeroth order concomitant gradient amplitudes may be different for positive and negative polarities due to the fact that the bipolar flow encoding lobes i.e., pulse areas are not typically equal in pulse width and amplitude in order to minimize echo time i.e., TE time. Therefore, because the zeroth order concomitant gradient generates a uniform spatially invariant additional magnetic field, there is a net phase accumulation for flow encoding gradients. This phase accumulation φ can be determined as:

$$\phi = \gamma \int_\tau B_{error,0th}(t)dt \quad (25)$$

where $\gamma = 267.552 \times 10^6$ rad/s/T is the gyromagnetic ratio, and τ is the total time of the flow encoding gradient. Taking the phase difference between the two acquisitions 208 and 210, the net phase is then $$\Delta\phi = \phi^+ - \phi^- = \gamma[\int_\tau B_{error,0th}^+(t)dt + \int_\tau B_{error,0th}^+(t)dt] \quad (26)$$

where the (+) and (−) sign denotes the positive and negative polarity of the bipolar flow encoding gradients. Eqn. (26) can further be modified by inserting the x-gradient value of zeroth order error field $B_{error,0th}$ from Eqn. (17). Thus, $$\Delta\phi = \frac{\gamma z_{0x}^2}{2B_0}\left[\int_\tau G_{x1}^2(t)dt + \int_\tau G_{x2}^2(t)dt\right] \quad (27)$$

where $G_{x1}$ and $G_{x2}$ are positive and negative polarity bipolar gradient waveforms respectively.

Figure 4:
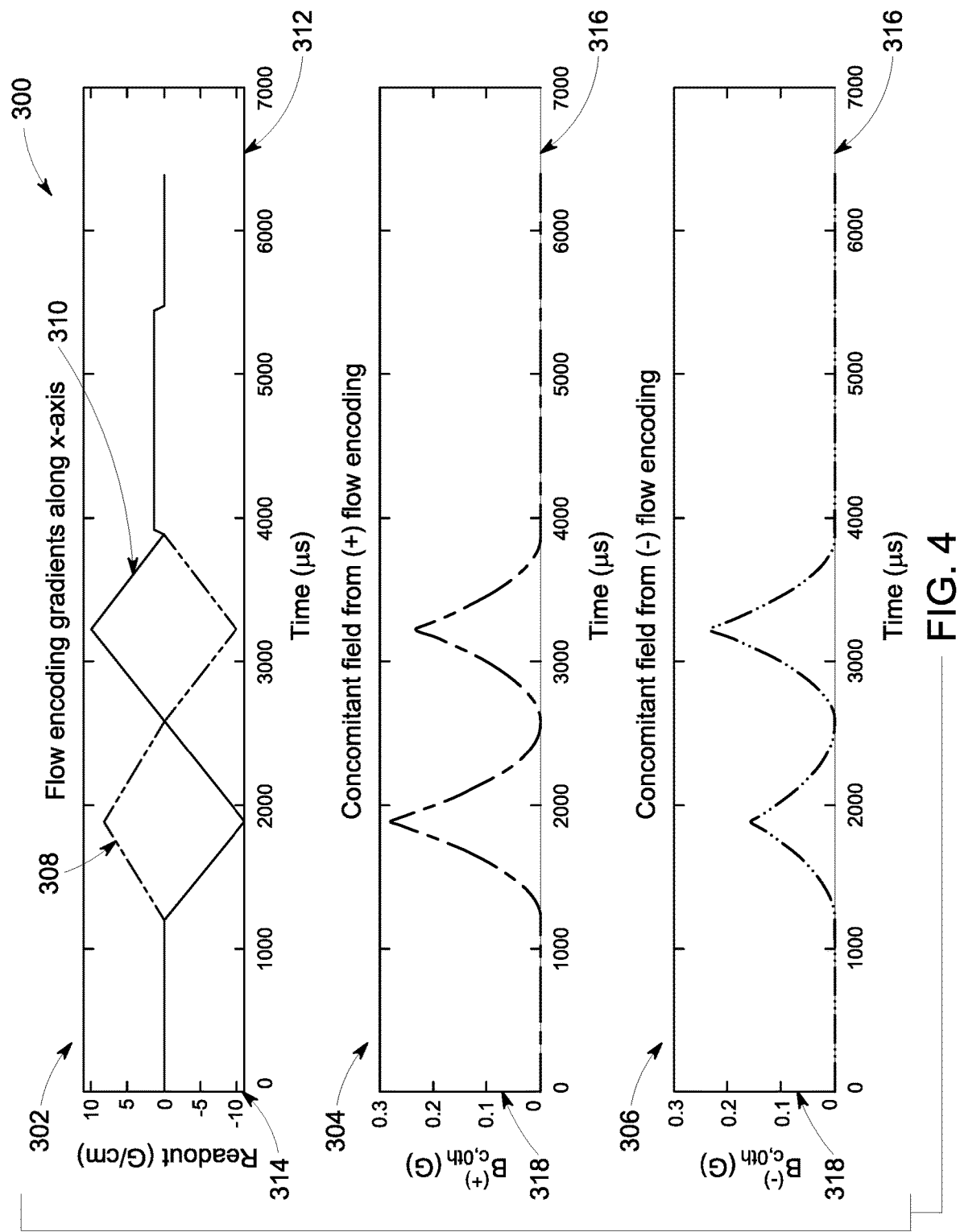
FIG. 4 is another graphical plot of bipolar phase contrast imaging gradient waveforms with associated zeroth order concomitant gradient fields, in accordance with an embodiment of the present technique.

FIG. 4 shows another graphical plot 300 of phase contrast imaging waveforms in accordance with an embodiment of the present technique. In FIG. 4, plot 302 shows a readout gradient direction with the bipolar gradient applied in the same direction; plot 304 shows the associated zeroth order concomitant gradient field $B_{c,0th}^+$ due to the positive bipolar encoding gradient 308 and plot 306 shows the associated zeroth order concomitant gradient field $B_{c,0th}^-$ due to the negative polarity bipolar encoding gradient 310. A horizontal axis 312 and a vertical axis 314 in plot 302 show time in microseconds and gradient amplitude in Gauss/cm, respectively. Further, a horizontal axis 316 and a vertical axis 318 in plots 304 and 306 show time in microseconds and field amplitude in Gauss, respectively. As with FIG. 3, the flow encoding gradient 302 is a bipolar gradient waveform that is toggled between a positive (+) polarity 308, and a negative (−) polarity 310. It should be noted that FIG. 4 shows the associated zeroth order concomitant field $B_{c,0th}^+$ and $B_{c,0th}^-$ from just the bipolar flow encoding gradient. This is because after taking the phase difference, the resulting zeroth order concomitant gradient field from the other gradient waveforms cancel out, as they do not change as the polarity of the bipolar gradients are changed.

Figure 5:
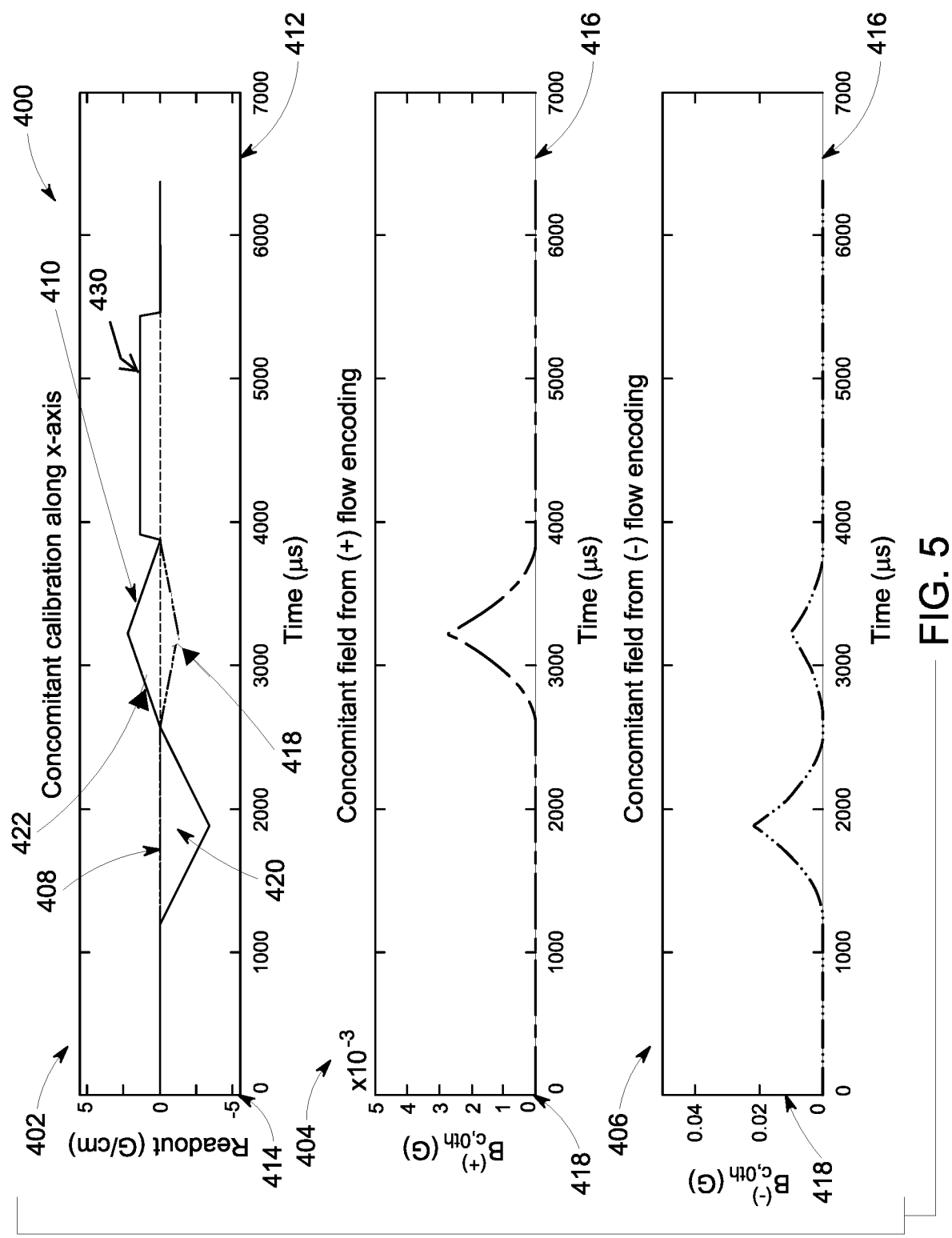
FIG. 5 is a graphical plot of single-sided bipolar gradient encoding type imaging waveforms, with associated zeroth order concomitant gradient fields, in accordance with an embodiment of the present technique.

Instead of using the standard flow encoding scheme as in FIG. 3, in one embodiment, a single-sided flow encoding type gradient waveform may be used to simply the calculations. If the flow encoding scheme in FIG. 3 is used, then the gradient flow encoding gradient amplitude may need to be increased in order to get a sufficient phase difference value. Thus, FIG. 5 shows a graphical plot 400 of single-sided bipolar encoding type imaging waveforms that is similar to that of flow encoding waveforms. Unlike flow encoding waveforms that calculates the bipolar waveform amplitudes and waveform pulse widths to match some velocity encoding values, the gradient waveform amplitude and pulse widths of the bipolar encoding waveform only needs to meet the criteria that the net gradient zeroth moment (or gradient amplitude×time) needs to equal that of gradient lobe 418. The area or zeroth moment of gradient lobe 418 is to provide the dephasing gradient area for the readout gradient 430. In FIG. 5, plot 402 shows a readout gradient waveform and toggled bipolar encoding waveforms; plot 404 shows the associated zeroth order concomitant gradient field $B_{c,0th}^+$ due to the positive bipolar encoding gradient 410 and plot 406 shows the associated zeroth order concomitant gradient field $B_{c,0th}^-$ due to the negative bipolar encoding gradient 408. A horizontal axis 412 and a vertical axis 414 in plot 402 show time in microseconds and gradient amplitude in Gauss/cm, respectively. Further, a horizontal axis 416 and a vertical axis 418 in plots 404 and 406 show time in microseconds and field amplitude in Gauss, respectively. As with FIG. 3, the bipolar encoding gradient shown in 402 is a bipolar gradient waveform that is toggled between a positive (+) polarity 408, and a negative (−) polarity 410. However, unlike FIG. 3, the positive polarity bipolar gradient waveform 408 has only one lobe, a negative lobe 418 to provide the dephasing gradient area for the readout gradient in the x-direction. Further, the negative polarity bipolar gradient waveform 410 has two lobes, a negative lobe 420 followed by a positive lobe 422.

If the gradients are applied in the y-direction (i.e., along the phase-encoding direction) instead of x-direction as shown in FIG. 5, the negative (−) encoding would have a zero gradient amplitude. Similarly, if the gradients are applied gradient in the z-direction (slice encoding direction), the negative (−) encoding would have only the slice rephasing gradient. The positive (+) polarity encoding gradient generally has a net gradient area (zeroth moment) equal to the area required to dephase spins prior to the readout gradient (x-direction), the net phase encoding gradient area or zero gradient area (y-direction), or the gradient area required to rephase the spins for the slice selection gradient (z-direction).

It can be seen from Eqn. (27), that the $z_{0x}^2$ term is a constant term pulled outside of the integral and a single measurement of a bipolar gradient $G_x$ can directly determine the value of that constant. However, to better account for other miscellaneous errors, it is preferable to varying the amplitude of the applied bipolar gradient $G_x$ (bipolar gradient 420), collecting a series of measurements, and data fitting the results to Eqn. (27) to minimize the effects of noise or spatially varying eddy currents. This is accomplished by using the single-sided approach to measure the phase difference as shown in FIG. 5.

Figure 6:
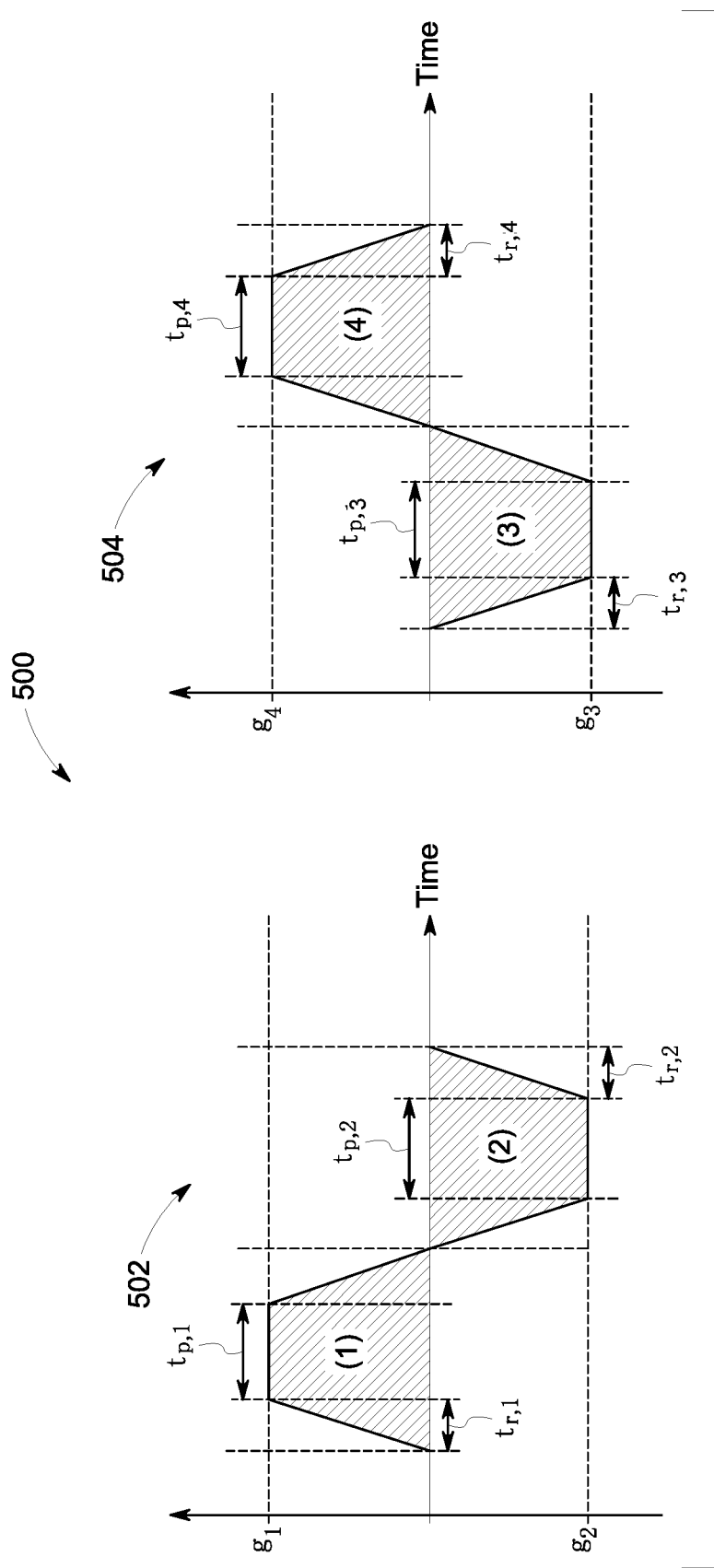
FIG. 6 is a graphical plot of bipolar gradient pulse diagrams of different polarity, in accordance with an embodiment of the present technique.

FIG. 6 shows a graphical plot 500 of gradient waveform diagrams in accordance with an embodiment of the present technique. Plot 500 shows a positive (+) polarity bipolar encoding gradient 502, and a negative (−) polarity bipolar encoding gradient 504. If we denote the gradient amplitudes, pulse widths, and waveform ramp times of the (+) polarity encoding gradient 502 as $g_1$, $g_2$, $t_{p;1}$, $t_{p;2}$, $t_{r;1}$, $t_{r;2}$ and that for the (−) polarity encoding gradient 504, $g_3$, $g_4$, $t_{p;3}$, $t_{p;4}$, $t_{r;3}$, $t_{r;4}$ the resulting phase due to zeroth order concomitant fields from the bipolar gradients are $$\phi^0(+) = \frac{\gamma z_{0x}^2}{2B_0}\int(g_1^2(t) + g_2^2(t))dt \quad (28)$$
$$= \frac{\gamma z_{0x}^2}{2B_0}\left(g_1^2\left[t_{p,1} + \left(\frac{2}{3}\right)t_{r,1}\right] + g_2^2\left[t_{p,2} + \left(\frac{2}{3}\right)t_{r,2}\right]\right)$$

and $$\phi^0(-) = \frac{\gamma z_{0x}^2}{2B_0}\int(g_3^2(t) + g_4^2(t))dt \quad (29)$$
$$= \frac{\gamma z_{0x}^2}{2B_0}\left(g_3^2\left[t_{p,3} + \left(\frac{2}{3}\right)t_{r,3}\right] + g_4^2\left[t_{p,4} + \left(\frac{2}{3}\right)t_{r,4}\right]\right)$$

It should be noted that the preceding analysis is only for an x-gradient axis, but similar analysis can be conducted for the y- and z-gradient axes. For determination of the gradient coil parameters, the proposed method, as mentioned earlier with respect to FIG. 5, sets $g_1=0$, so that there is only one lobe for the positive polarity gradient. The phase difference is then $$\Delta\phi = \left(\frac{\gamma}{2B_0}\right)z_{0x}^2\left\{g_3^2\left[t_{p,1} + \left(\frac{2}{3}\right)t_{r,1}\right] + (g_4^2 - g_2^2)\left[t_{p,2} + \left(\frac{2}{3}\right)t_{r,2}\right]\right\} \quad (30)$$

-continued $$= \left(\frac{\gamma}{2B_0}\right) z_{0x}^2 (g_3^2 t_{pw,1} + (g_4^2 - g_2^2) t_{pw,2})$$

where $$t_{pw,1} = \left[t_{p,1} + \left(\frac{2}{3}\right) t_{r,1}\right] \text{ and } t_{pw,2} = \left[t_{p,2} + \left(\frac{2}{3}\right) t_{r,2}\right]$$

where $g_3$ is varied from $-g_t, \ldots, +g_t$ in a plurality of increments such that the maximum phase difference is small such that $|\Delta\phi|<2\pi$, i.e., to avoid aliasing. In Eqn. (30), we further assume that the pulse widths and ramp times of bipolar encoding gradient 502 is the same as in bipolar encoding gradient 504 to simplify to Eqn. (30). We note that the same analysis can be performed if the pulse widths and ramp times of bipolar encoding gradients 502 and 504 are not the same, without loss of specificity. As such, in Eqn. (30), we set $t_{p;3}=t_{p;1}$, $t_{p;4}=t_{p;2}$, $t_{r;3}=t_{r;1}$, and $t_{r;4}=t_{r;2}$. It should be noted that $g_4$ is related to $g_3$ by:

$$g_4 = \frac{A_2 - g_3(t_{p,1} + t_{r,1})}{(t_{p,2} + t_{r,2})} \quad (31)$$

where $A_2=g_3(t_{p,2}\ t_{r,2})$ is the area or zeroth moment of the readout dephaser gradient 430. Similarly, to determine the correct value of $z_{0y}$, the bipolar gradient waveforms are applied to the y-axis (phase encoding direction) and the phase difference is then determined as:

$$\Delta\phi = \left(\frac{\gamma z_{0y}^2}{2B_0}\right)(g_3^2 t_{pw,1} + g_4^2 t_{pw,2}) \quad (32)$$

as $g_1=g_2=0$ for the bipolar waveforms applied in the phase encoding direction. Consequently, $z_{0y}$ can be determined from Eqn. (32) from the fit of the measured phase difference as the gradient amplitudes, $g_3$ and $g_4$ are varied.

Eqn. (32) assumes that the phase encoding gradients are separated from the bipolar waveforms (i.e., not combined as in the method to minimize TE time). As such, both $z_{0x}$ and $z_{0y}$ can be independently determined. Further, Eqn. (32) assumes that for a specific scan plane orientation, the frequency readout direction remains fixed while the bipolar encoding directions changes from the readout direction to the phase encoding direction. However, if the frequency direction also shifts with the bipolar encoding directions, then either Eqn. (30) or Eqn. (32) can be used to determine $z_{0x}$ and $z_{0y}$. It is also noted that if the phase encoding gradients are not separated out from the bipolar waveforms, the analysis of Eqn. (28), (29), and (32) still holds as the associated concomitant gradient field effects from the phase encoding gradient lobes cancel out in the phase difference. This underscores the advantage of the present technique as it eliminates or substantially reduces the concomitant contributions of gradient waveforms other than that of the bipolar encoding gradient waveforms.

As an example, as $z_{0x}$ and $z_{0y}$ offsets are relevant only if a gradient waveform is applied in the physical x and/or y axes, and the scan protocol is for an axial plane acquisition. To determine $z_{0x}$, the frequency encoding direction is set to the right/left (R/L) direction, and the bipolar encoding is also set to the R/L direction. In this manner, the gradients, $g_2$, $g_3$, and $g_4$, are applied along the x-axis (with $g_1=0$). To determine $z_{0y}$, the frequency encoding direction in an axial plane acquisition is set to the anterior/posterior (A/P) direction, together with the bipolar encoding gradient also in the A/P direction. The gradients, $g_2$, $g_3$, and $g_4$, are now applied along the y-axis. Hence, fitting the measurements to Eqn. (30) will allow the determination of $z_{0y}$. The same process is relevant if the single-sided bipolar waveform is applied to the phase-encoding direction without changing the frequency encoding direction, where the measurements would then be fitted to Eqn. (32).

Figure 7:
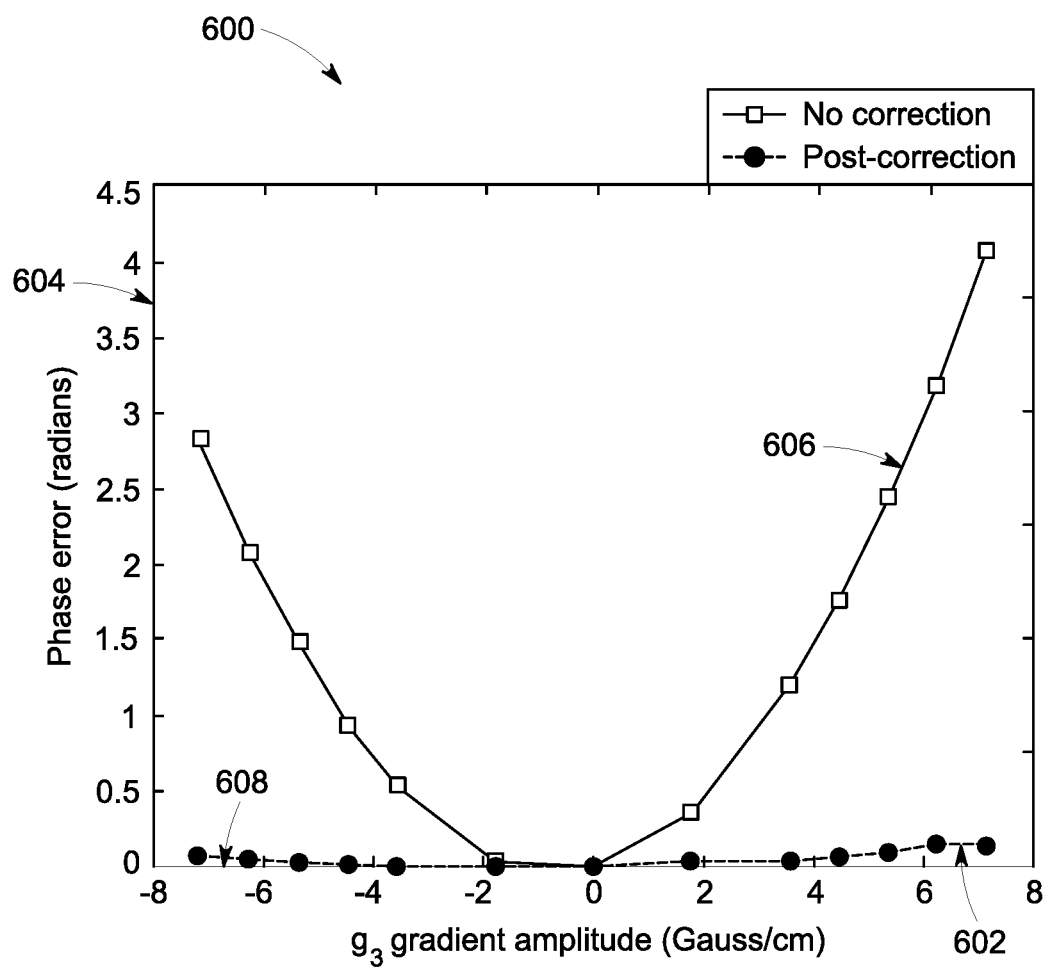
FIG. 7 is a graphical plot of a measured phase error of the phase difference acquisition, in accordance with an embodiment of the present technique.

FIG. 7 shows a graphical plot 600 of a measured phase error or phase difference as a function of gradient amplitude $g_3$ in accordance with an embodiment of the present technique. In the graphical plot 600, horizontal axis 602 represents $g_3$ gradient amplitude in gauss/cm, and vertical axis 604 represents measured phase difference or phase error in radians. The plot includes a first curve 606 which is without concomitant field correction and a second curve 608 which is with concomitant field correction.

As can be seen from curve 606, several measurements of gradient amplitudes of $g_3$ as it is varied from $g_3=-7, \ldots, +7$ Gauss/cm, and the corresponding phase difference or phase errors are made. Since the measurement is of a stationary phantom, a zero phase difference is expected. However, due to the concomitant gradient field effects, a non-zero phase difference is measured. This non-zero phase difference constitutes a phase error due to concomitant gradient field effects. By fitting the measured data points to Eqn. (30), the gradient coil offset, $z_{0x}$ can be determined by using typical data fitting methods, such as least-squares fitting or polynomial fitting. In a similar fashion, with adjustments to the axis of the applied bipolar gradients, $z_{0y}$ can be determined by fitting the corresponding measured data points to Eqn. (31) or Eqn. (32), depending on whether if the readout gradient direction is changed. Since the gradient coil constants, $z_{0x}$ and $z_{0y}$ are also relevant to the correction of first order concomitant gradient effects (as noted in Eqn. (20), it is sufficient to perform system calibration using the equations only for the zeroth order concomitant field effects. After the determination of gradient coil constants $z_{0x}$ and $z_{0y}$, gradient compensating waveforms that compensate for the concomitant field effects are generated for both zeroth and first order corrections. Curve 608 shows that after compensating for the concomitant field, the phase error or phase difference remains about zero radians.

The technique described above was evaluated in an experimental study. The experiment was performed on a GE MR750 3.0 T MRI scanner (GE Healthcare, Waukesha, Wis.) with a Microstructure Anatomy Gradient for Neuro-imaging with Ultrafast Scanning (MAGNUS) gradient coil ($G_{max}=200$ mT/m, and $SR_{max}=500$ T/m/s) replacing the standard whole-body gradient and transmit/receive RF coil. Similar results were obtained with a Compact 3T head-gradient coil ($G_{max}=80$ mT/m, and $SR_{max}=700$ T/m/s) with asymmetrical transverse gradient coils. In the MAGNUS system with asymmetrical transverse gradient coils and symmetrical z-gradient coil, the peripheral nerve stimulation threshold is substantially higher than in whole-body gradient systems, allowing the use of the maximum slew rate for echo planar imaging (EPI). A 32-channel receive coil was used in all studies (NOVA Medical, Wilmington, Mass.). A 14-cm diameter spherical oil phantom was placed in the coil and allowed to settle for several hours for the phantom to equalize in temperature in the magnet bore and also to minimize any thermal convection.

A standard, ungated gradient echo phase contrast acquisition was modified and used in the experiments. Scan parameters used were: 24-cm image field-of-view; 10-mm slice thickness; 256×128 matrix; TR (repetition time)=20 ms; 15° flip angle; axial plane; frequency direction=R/L; ±15.65 kHz bandwidth; VENC (velocity encoding value)=100 mm/s. Note that the VENC value is used only to establish the bipolar encoding gradient waveform pulse widths and ramp times. With a minimum TE (echo time) setting, this resulted in TE=6.4 ms. Table 1 lists the pulse widths of the resulting waveforms corresponding to that in FIG. 6. The amplitudes of $g_3$ were varied between −7, . . . , +7 G/cm, with the values of $g_4$ changed accordance to Eqn. (31). The mean signal intensity in a region-of-interest taken at the center of the phase difference image was recorded for each value of $g_3$. The maximum amplitude of $g_3$ was such that the maximum phase difference was <2π, −π<Δφ<+π, to avoid aliasing.

TABLE 1

| Waveform | Amplitude (G/cm) | Ramp time (µs) | Flat top time (µs) |
|---|---|---|---|
| $g_1$ | +8.10 | 700 | 4 |
| $g_2$ | −9.87 | 672 | 4 |
| $g_3$ | −10.84 | 700 | 4 |
| $g_4$ | +9.87 | 672 | 4 |

Figure 8:
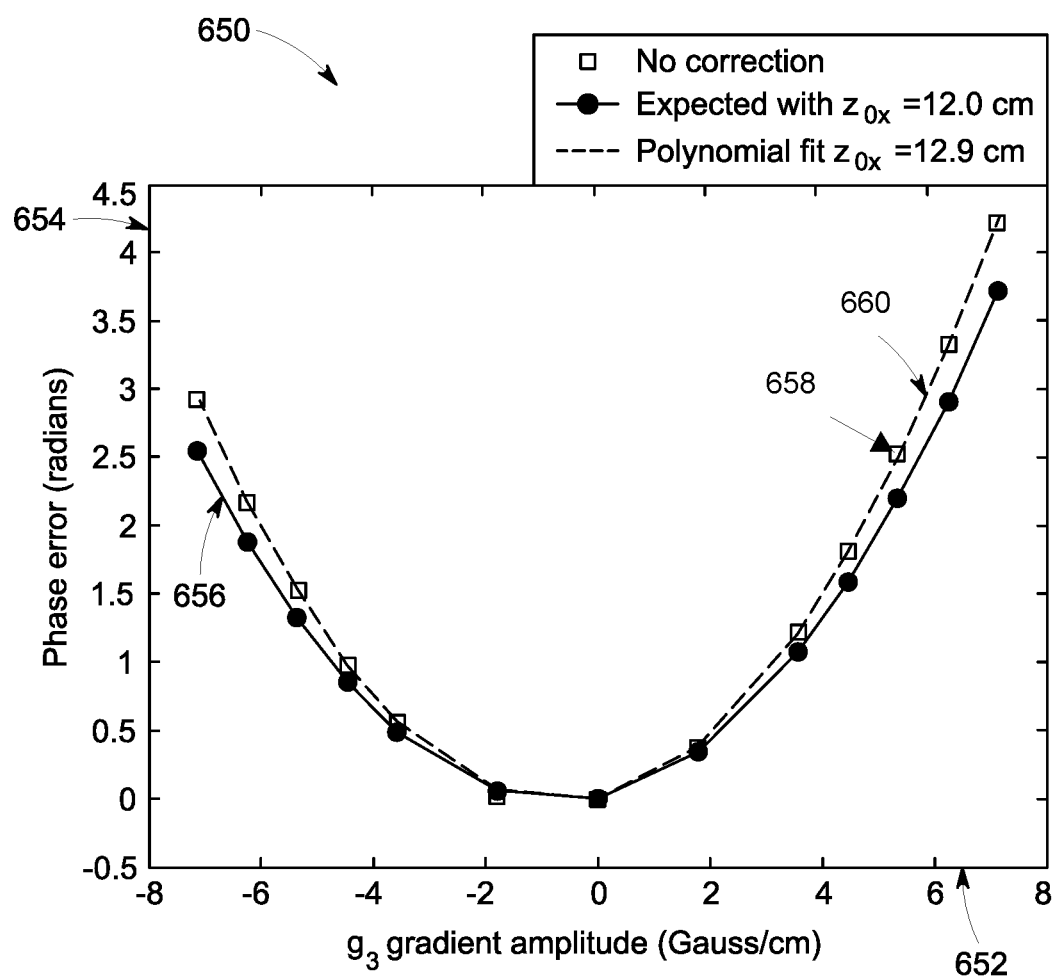
FIG. 8 is a graphical plot of experimental results, in accordance with an embodiment of the present technique.

The results of the above experiment are shown in a graphical plot 650 of the FIG. 8. In the graphical plot 650, horizontal axis 652 represents $g_3$ gradient amplitude in Gauss/cm and vertical axis 654 represents phase error or phase difference in radians. A first plot 656 which is an expected phase error or phase difference predicted using a theoretical design or default gradient coil constant $z_{0x}$=12.0 cm, and a second plot 658 which is actual phase error or phase difference that is determined from measurements (without concomitant field correction). The dashed line 660 shows the result of a second order polynomial fit of Eqn. (30) to the measured data 658. It shows that from measurements, the actual gradient coil constant $z_{0x}$=12.9 cm, which is different from that determined from the theoretical design or electromagnetic analysis. In general, as described earlier, during installation of the gradient coil, the z position of the gradient coil may vary, and this introduces error in the concomitant gradient field correction factors if default design parameters are used. This is in addition to the manufacturing tolerances where additional errors could be introduced. Therefore, the calibration of the concomitant gradient correction factors post installation is necessary.

As can be seen from plot 650, the measured phase error or phase difference as a function of $g_3$ amplitude, increased with increasing amplitude of $g_3$. It can be noted that when the default or design gradient coil constant, $z_{0x}$, was used in Eqn. (30), the expected phase error or phase difference (i.e., curve 656) under-estimated the actual measurements (i.e., curve 658). This indicated that the default value of $z_{0x}$ of 12 cm was incorrect. Fitting the measured data to Eqn. (30), the gradient offset, $z_{0x}$ can be determined by using typical data fitting methods, such as least-squares fitting of a second order polynomial, $y=a_1 x^2+a_2 x+a_3$. With the fit of the coefficient of the quadratic term in $g_3$ given as $$z_x^0 = \sqrt{a_1\left(\frac{2B_0}{\gamma}\right)\left(t_{pw,1}+t_{pw,2}\left(\frac{t_{p,1}+t_{r,1}}{t_{p,2}+t_{r,2}}\right)^2\right)^{-1}} \quad (33)$$

and resulted in $z_{0x}$=12.9±0.2 cm. This shows that the default value of $z_{0x}$ of 12 cm was off by about 1 cm. It should be noted that instead of second order polynomial, $z_{0x}$ or $z_{0y}$ can also be determined from the fit to the linear or constant term. However, the confidence interval of the fit for each of the coefficients of the second order polynomial can be used as a guide as to which fitted value is most accurate.

Figure 9:
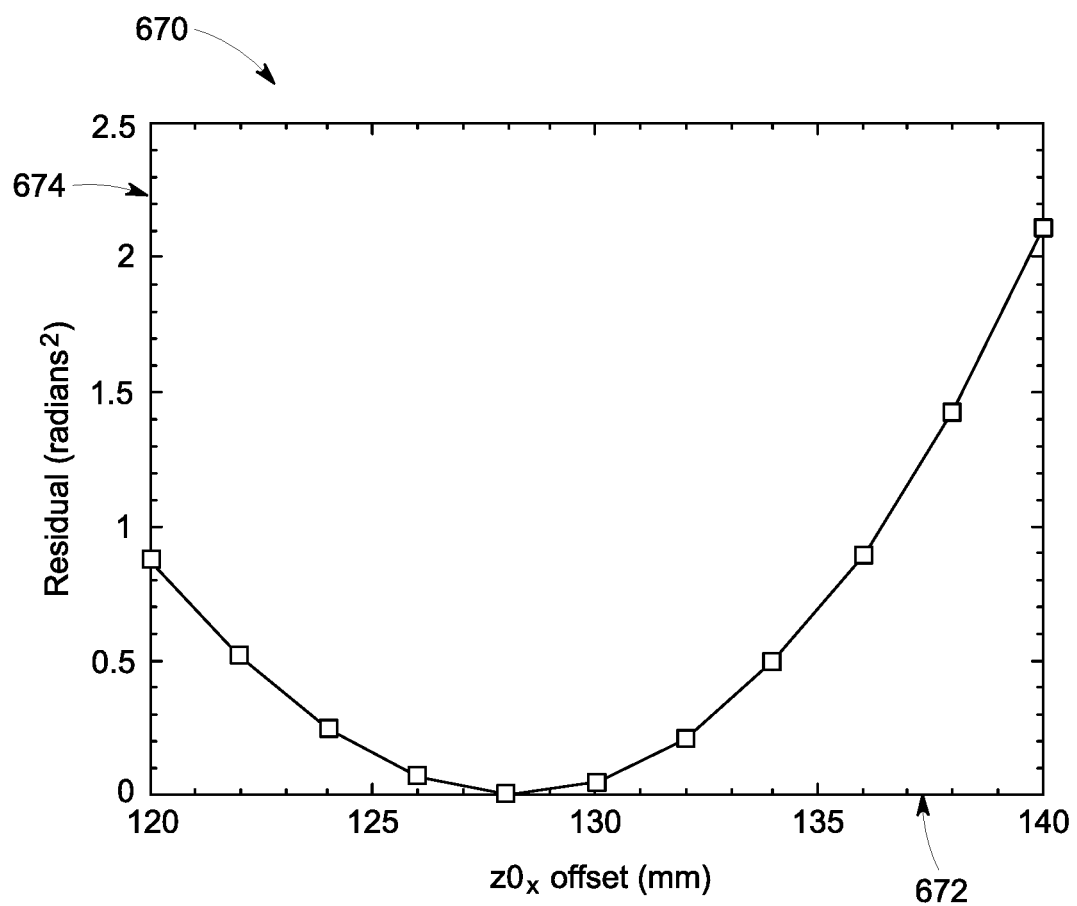
FIG. 9 is a graphical plot of a residual error in the phase error as a function of the value of the offset constant for the x-gradient axis, in accordance with an embodiment of the present technique.

FIG. 9 shows a graphical plot 670 of residual error in the phase difference measurements from the expected zero phase. In the graphical plot 670, a horizontal axis 672 represents gradient correction offset $z_{0x}$ in mm and vertical axis 674 represents residual error in the phase error in radians². In general, if the offsets, $z_{0x}$ or $z_{0y}$ are far off the correct value, the applied correction, as shown in FIG. 8, will not be effective and a large error in the post-corrected phase is obtained. However, in the example provided, varying $z_{0x}$ by ±3 mm produces a fairly narrow minima as seen in plot 670. This shows that the above technique in determining gradient coil correction constants is fairly accurate.

The importance of determining the correct values of the gradient coil constants, $x_0$, $y_0$, $z_{0x}$, and $z_{0y}$ is in the use of these constants in the concomitant gradient corrections. Correction of the concomitant gradient effects can be performed by adjusting the frequency of the MRI receiver and transmitter (for the zeroth order correction) or by gradient pre-emphasis for the first order effects. As an example, referring to first-order correction of Eqn. (20) for asymmetrical gradients, pulsing the x gradient with an amplitude of $G_x$ results in a concomitant field that is spatially varying in z direction such that the error field is $$B_{error,1st} \approx \frac{G_x^2 z_{0x}}{B_0} z \quad (34)$$

where $$\frac{G_x^2 z_{0x}}{B_0}$$

is essentially equivalent w an applied gradient in the z-direction. Hence, if an x gradient is applied, then the concomitant correction would require a small compensatory gradient pre-emphasis applied to the z gradient such at any time, t, the gradient waveforms that are played out, denoted as $G_{x,y,z}^{1st}(t)$ are $$G_x^{1st}(t) = G_x(t) \quad (35)$$

$$G_y^{1st}(t) = 0$$

$$G_z^{1st}(t) = -\frac{G_x^2(t) z_{0x}}{B_0}$$

where $G_x(t)$ is the gradient amplitude command and is typically given by $I^c(t) \times \eta_{x,y,z}$, $\eta_{x,y,z}$ being the coil gain or coil efficiency for the x, y, and z gradient coils respectively, and $I^c(t)$ is the command current to generate the targeted gradient field amplitude. As can be seen from Eqn. (34), for the standard gradient amplitude command $G_x(t)$, a compensatory gradient pre-emphasis −

$$-\frac{G_x^2(t)z_{0x}}{B_0}$$

is applied to the z gradient to correct for the first order concomitant gradient field effect.

Similarly, for a desired y gradient of $G_y$, the applied gradient with pre-emphasis is $$G_x^{1st}(t) = 0 \qquad (36)$$
$$G_y^{1st}(t) = G_y(t)$$
$$G_z^{1st}(t) = -\frac{G_y^2(t)z_{0y}}{B_0}$$

In other words, for the standard gradient amplitude command $G_y$(t) a compensatory gradient pre-emphasis –

$$-\frac{G_y^2(t)z_{0y}}{B_0}$$

is applied to the z gradient. Further, it should be noted that for a desired z gradient of $G_z$, the pre-emphasis can be neglected if there are no other gradients applied simultaneously. However, if there is an applied gradient in the x and y directions, then the overall corrections for each time point is $$G_x^{1st}(t) = G_x(t) + \frac{G_x(t)G_z(t)z_{0x}}{2B_0} \qquad (36)$$
$$G_y^{1st}(t) = G_y(t) + \frac{G_y(t)G_z(t)z_{0x}}{2B_0}$$
$$G_z^{1st}(t) = G_z(t) - \frac{G_y^2(t)z_{0y}}{B_0} - \frac{G_x^2(t)z_{0x}}{B_0}$$

The additional terms in Eqn. (36) (other than $G_x$(t), $G_y$(t) and $G_z$(t) represent the compensation or correction terms. In other words, compensatory gradient waveforms are applied to a gradient coil such that a concomitant correction gradient field is generated in the same direction as the concomitant gradient field.

Figure 10A:
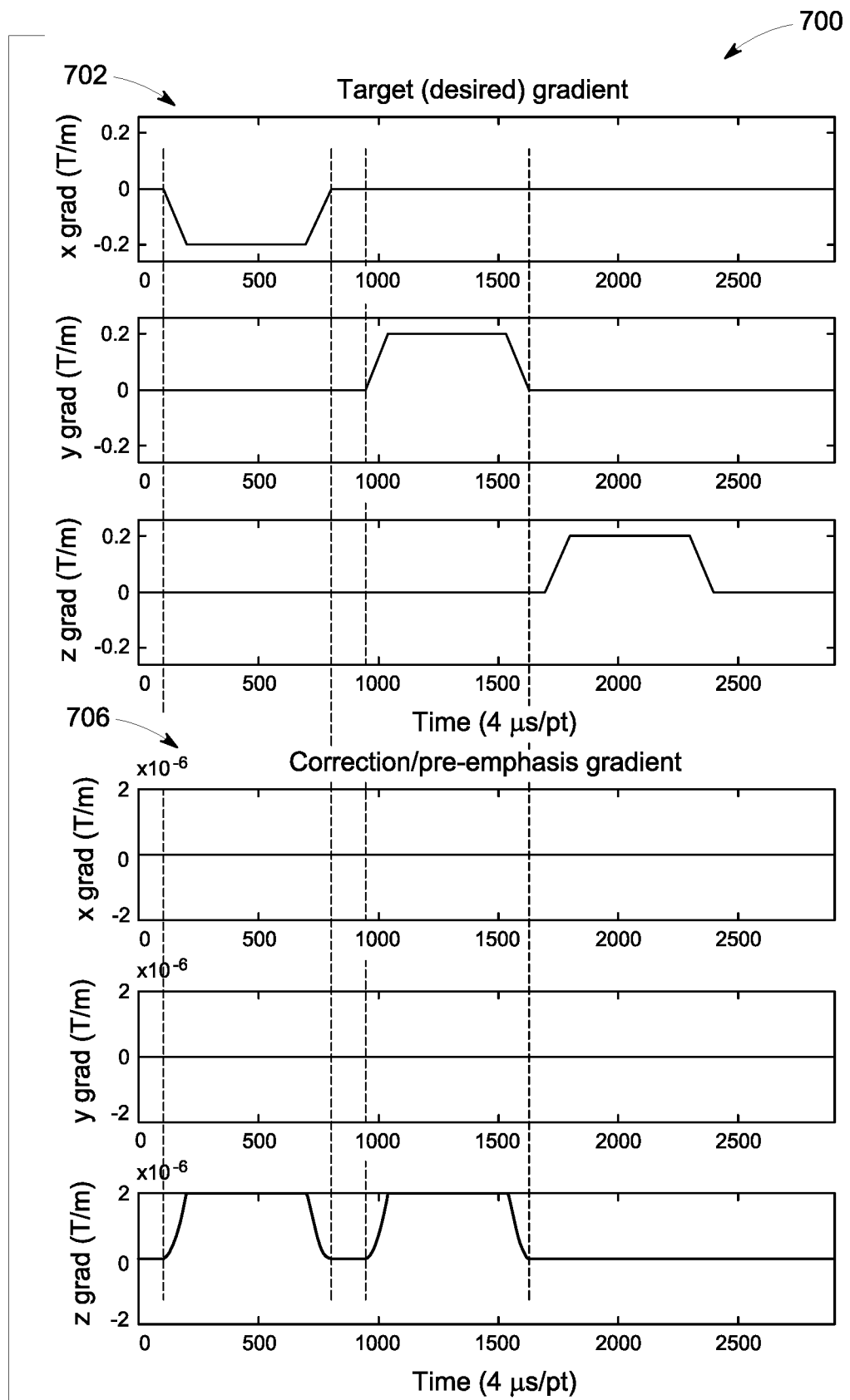
FIGS. 10A and 10B are graphical plots of desired or applied gradient waveforms together with the compensatory fields to reduce the first order concomitant gradient field effects, in accordance with an embodiment of the present technique.
Figure 10B:
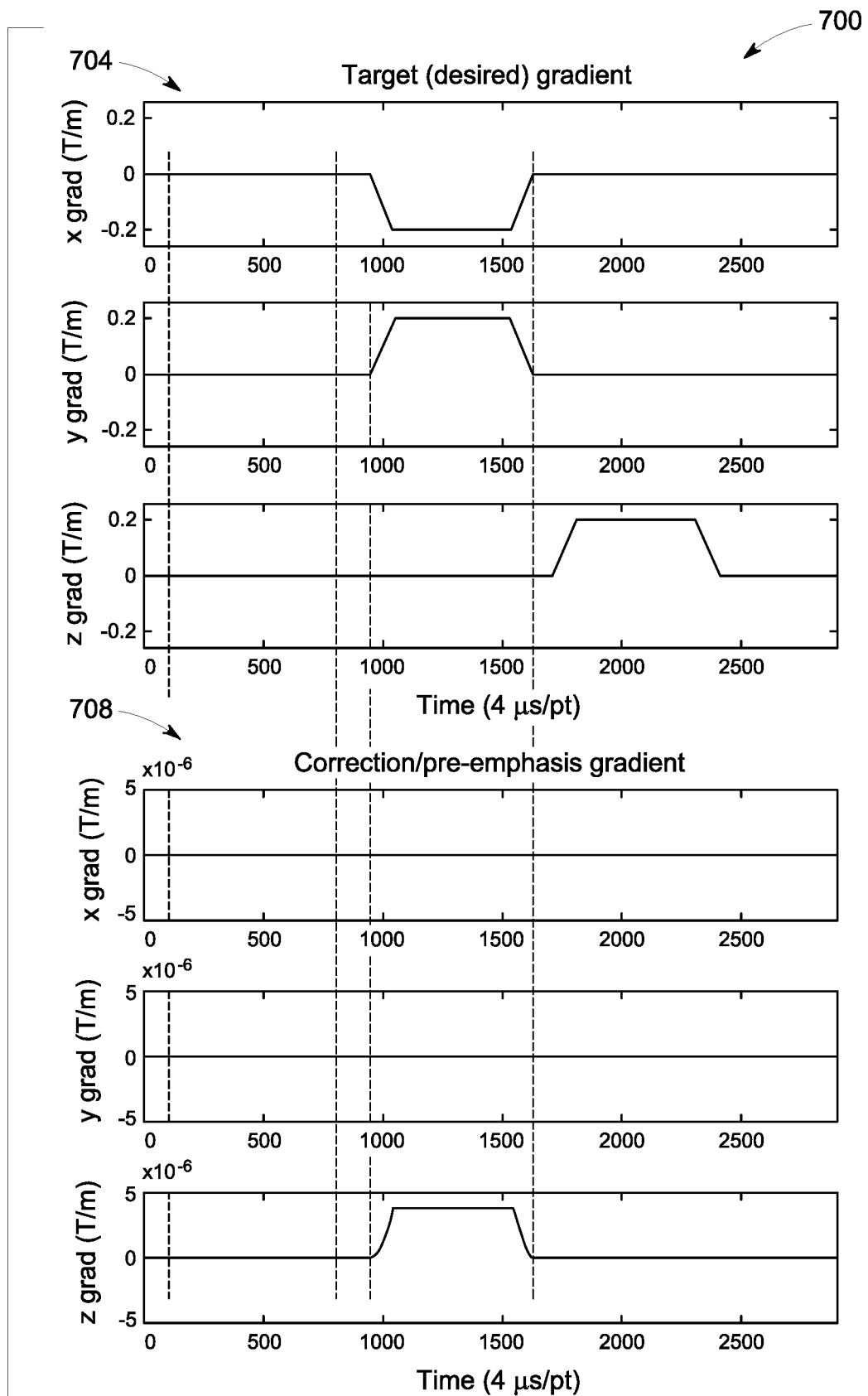

FIGS. 10A and 10B show a graphical plot 700 of gradient waveforms in accordance with an embodiment of the present technique. Specifically, in FIGS. 10A and 10B, plots 702 and 704 represents desired x, y and z gradient waveforms that needs to be applied to the gradient windings of the MR machine i.e., target gradients that are needed to for normal operation. However, as discussed above, with the present technique a correction or pre-emphasis gradient is applied in order to correct the concomitant gradient effects. These pre-emphasis gradients are shown in corresponding plots 706 and 708. It should be noted that the pre-emphasis gradients of plots 706 and 708 are applied to the z-gradient for correction of first order concomitant field effect.

Figure 11:
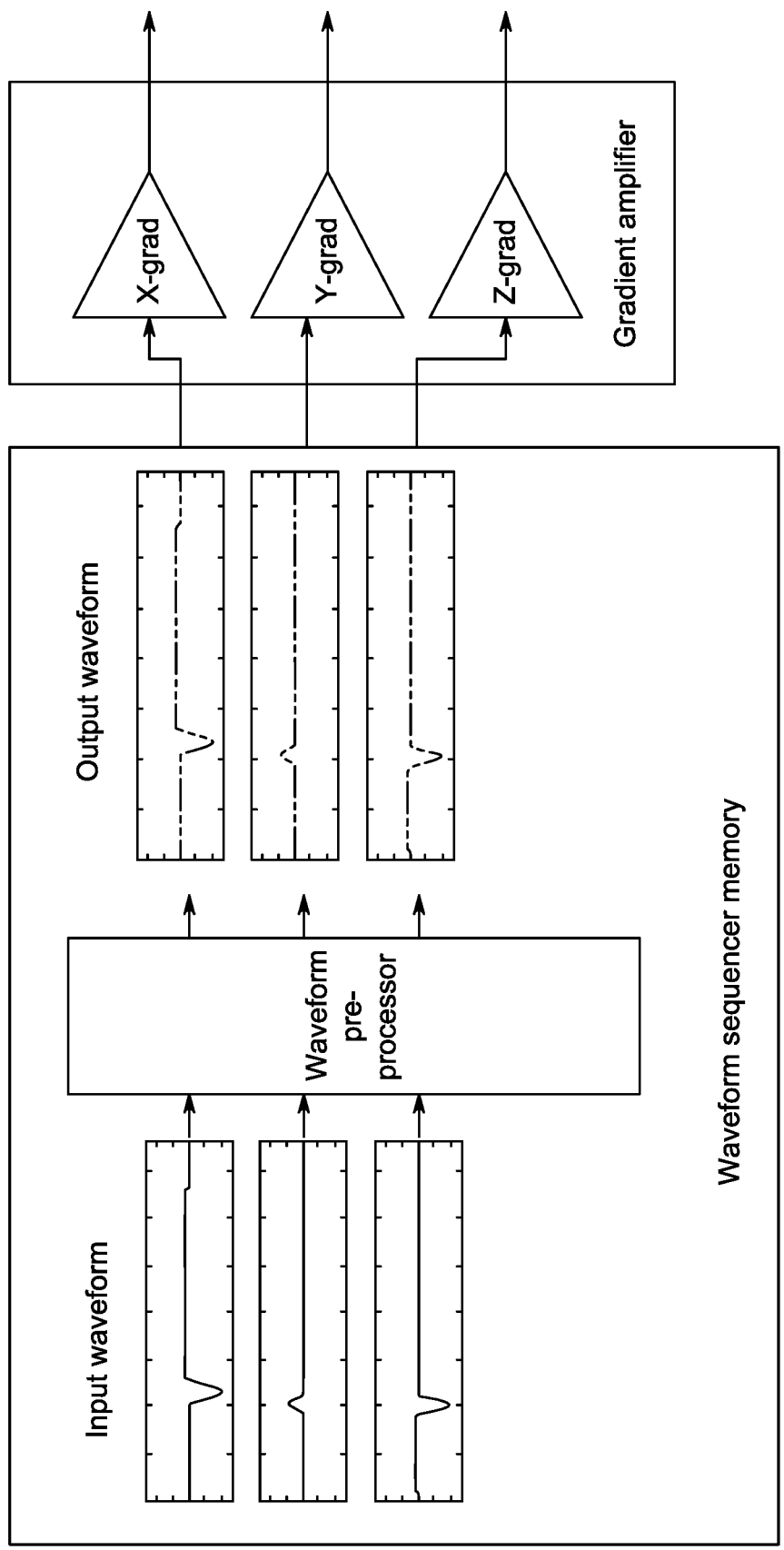
FIG. 11 is a schematic diagram of a system for correcting gradient waveforms, in accordance with an embodiment of the present technique.
Figure 12:
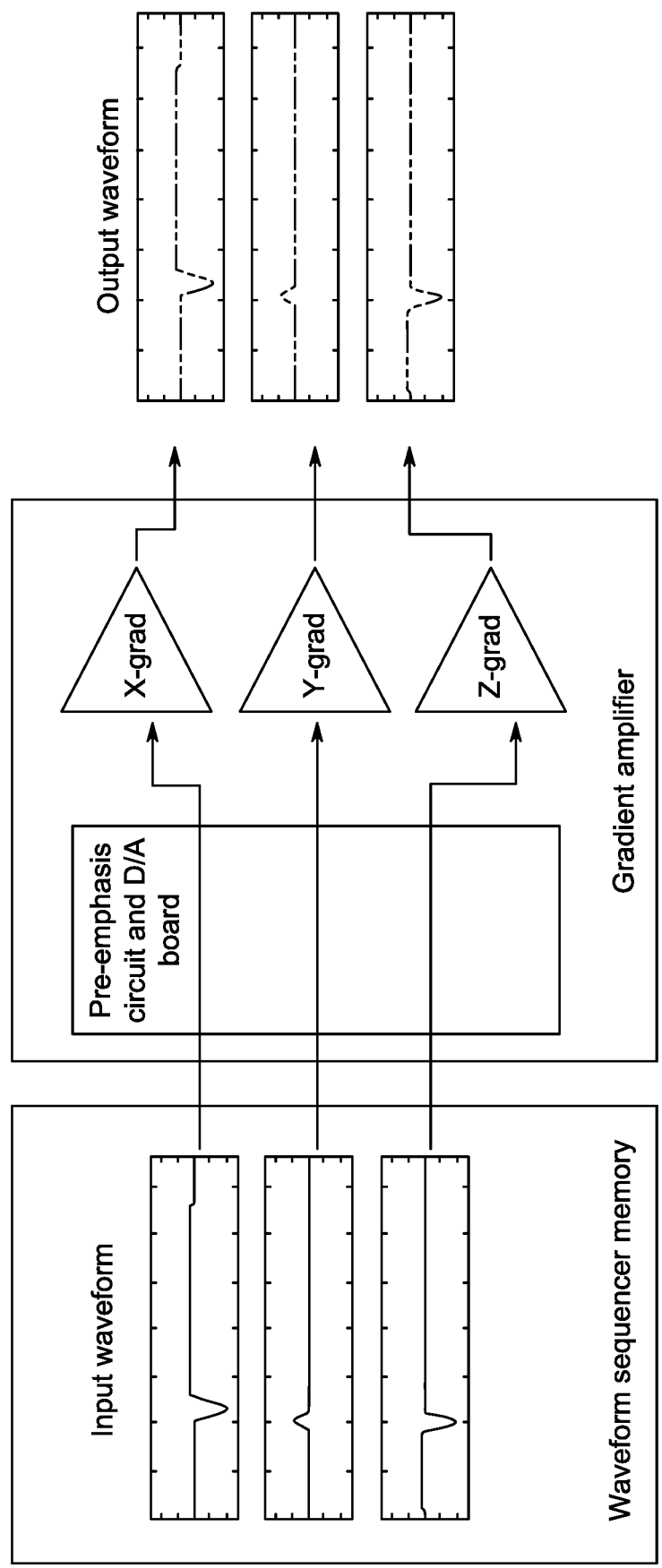
FIG. 12 is a schematic diagram of a system for correcting gradient waveforms, in accordance with an embodiment of the present technique.

Given that we have a programmable waveform with some digital resolution in time and amplitude, the digital command sent to the gradient amplifiers are essentially that of Eqn. (36). The corrected waveforms can be pre-calculated in a typical MRI pulse sequence memory as shown in FIG. 11 or the correction can also be performed by a dedicated pre-emphasis board that performs the correction of Eqn. (36) as a system input/controller transfer function as shown in FIG. 12. In other words, the system for correcting gradients in FIG. 11 utilizes stored gradients waveforms which are combination of target gradient waveforms as well as gradient correction waveforms. The system for correcting gradients in FIG. 12 modifies the target gradient waveforms in real time by applying the gradient correction factors using a dedicated circuit board.

It should be noted that the zeroth order concomitant gradient field (Eqn. (17)) effects can be corrected by changing the MRI transmitter and receiver frequency specification in a waveform control board. This can be done as a real-time frequency correction using an external FPGA (field programmable gate array) board. In this case, for applied gradients in the x and y directions, the correction for 0th order is a frequency adjustment such that $$\Delta f_0^{corr} = -\frac{\gamma}{4\pi B_0}[G_x^2 z_{0x}^2 + G_y^2 z_{0y}^2] \qquad (37)$$

where $\Delta f_0^{corr}$ is RF frequency offset in units of Hz used to compensate for zeroth order concomitant field.

In one embodiment, the zeroth order concomitant gradient correction can also be performed as a pre-calculation in the frequency pulse sequencer board. In which case, the correction can be applied as a time-varying frequency offset during the slice selection or readout gradient (i.e., during the data acquisition window), if there is an applied gradient in the x or y direction during those pulse sequence periods. This type of correction is useful if the amplitude of the applied gradient is sufficiently large such that the frequency offsets, as given in Eqn. (36), exceed the correction range of the FPGA. In another embodiment, if the applied gradients are outside of the slice selection radiofrequency pulse window or the data acquisition period, the accumulated phase can be added to the receiver offset in the waveform pulse sequence generator.

Figure 13:
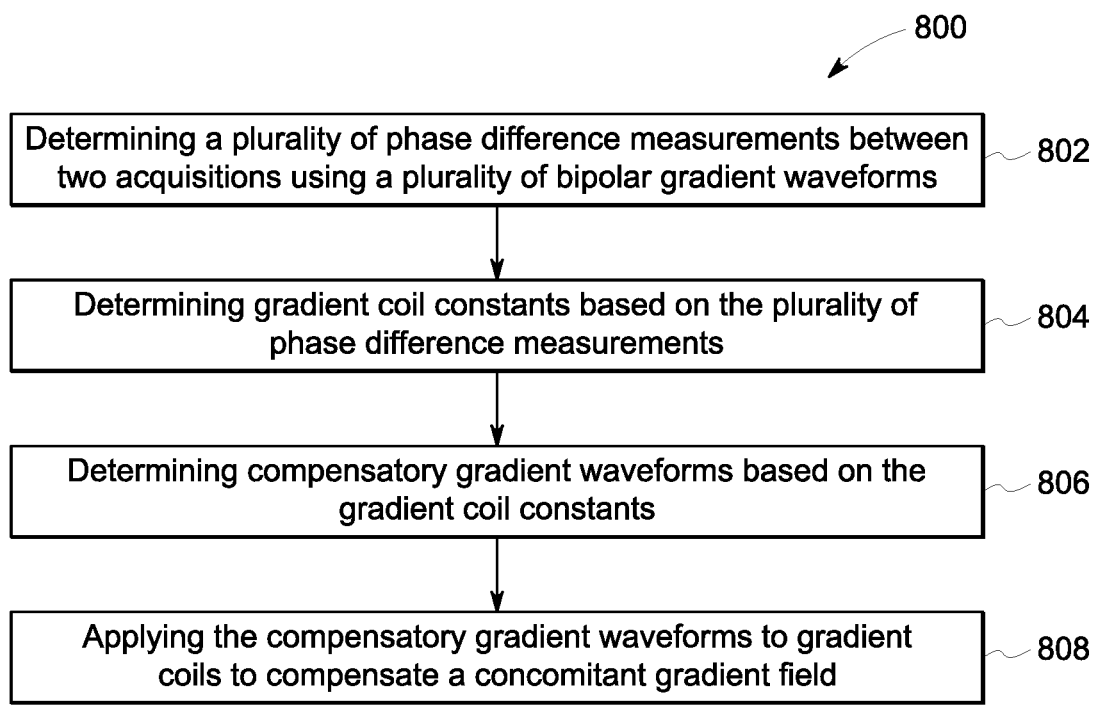
FIG. 13 is a flow chart depicting a method for correcting concomitant gradients effects in a MRI system, in accordance with an embodiment of the present technique.

FIG. 13 is a flow chart 800 depicting a method for correcting concomitant gradients effects in an MRI system. The method includes determining a plurality of phase difference measurements between two acquisitions using a plurality of bipolar gradient waveforms at step 802. For example, a first bipolar gradient waveform is applied to a first gradient, such as an x gradient, and then a second bipolar gradient waveform is applied to a second gradient, such as a y gradient, independently. The first and second bipolar gradient waveforms include two gradient lobes of positive and negative polarities. It should be noted that at least one of the bipolar gradient waveforms in each acquisition is reduced to a single gradient lobe depending on whether the gradient coil is in a readout mode or a phase encoding mode.

Further, the plurality of phase difference measurements includes first phase difference measurements and second phase difference measurements corresponding to the x and y gradients respectively. At step 804, the method includes determining gradient coil constants based on the plurality of phase difference measurements. The gradient coil constants include a first gradient coil constant which is determined based on first phase difference measurements and a second gradient coil constant which is determined based on second phase difference measurements. The first and second gradient coil constants are determined by data fitting the first and second phase difference measurements to mathematical expressions corresponding to a phase difference generated by one of the zeroth order concomitant gradient field, first order concomitant gradient field or second order concomitant gradient field.

At step 806, compensatory gradient waveforms are determined based on the gradient coil constants. In one embodiment, the compensatory gradient waveforms compensate for a first order concomitant field and a second order concomitant field. In one embodiment, the compensatory gradient waveforms may be pre-calculated in an MRI pulse sequence memory. In another embodiment, the compensatory gradient waveforms may be calculated in real-time in a pre-emphasis board. Finally, the compensatory gradient waveforms are applied to gradient coils to compensate for a concomitant gradient field in step 808. The compensatory gradient waveforms are applied to the gradient coils in conjunction with target gradient waveforms. The method further includes correcting a third order concomitant gradient field in post-processing of acquisition data acquired after applying the compensatory gradient waveforms with target gradient waveforms. Further, a zeroth order component of the concomitant gradient field is corrected by adjusting a frequency of an MRI system receiver and transmitter.

One advantage of the present technique is that once the gradient coil constants are determined from the measurements, they can be loaded into the appropriate configuration file for accurate corrections for concomitant gradient effects. Further, the image quality can be improved when high amplitude gradient fields are applied in asymmetric gradient coils. Moreover, with the present technique, artifacts from improper insertion of asymmetric gradient coils can be identified quickly and corrective action can be taken. In addition, the technique also ensures that the gradient coil parameters are valid and applicable for a range of gradient amplitudes from +maximum to −maximum, through 0 amplitude.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for correcting concomitant gradient field effects in an magnetic resonance imaging (MRI) system, the method comprising:
   determining a plurality of first phase difference measurements between two acquisitions using a plurality of first bipolar gradient waveforms applied to a first gradient coil;
   determining a first gradient coil constant based on the plurality of first phase difference measurements;
   determining compensatory gradient waveforms based on the first gradient coil constant; and
   applying the compensatory gradient waveforms with target gradient waveforms to compensate for a concomitant gradient field.

2. The method of claim 1, wherein the first gradient coil is an asymmetric gradient coil.

3. The method of claim 1, wherein the compensatory gradient waveforms compensate for a first order component and a second order component of the concomitant gradient field.

4. The method of claim 1, wherein a second and third order components of the concomitant gradient field is corrected for in post-processing of acquisition data acquired after applying the compensatory gradient waveforms with target gradient waveforms.

5. The method of claim 1 further comprising determining a second gradient coil constant based on a plurality of second phase difference measurements between two acquisitions using a plurality of second bipolar gradient waveforms applied to a second gradient coil.

6. The method of claim 1, wherein the plurality of first bipolar gradient waveforms includes two gradient lobes of positive and negative polarities.

7. The method of claim 6, wherein at least one of the first bipolar gradient waveforms in each acquisition is reduced to a single gradient lobe depending on whether the first gradient coil is in a readout mode or a phase encoding mode.

8. The method of claim 6, wherein the gradient lobe of the plurality of first bipolar gradient waveforms which are not reduced to the single gradient lobe are varied in a step fashion such that the first phase difference is less than 2π.

9. The method of claim 1, wherein determining the first gradient coil constant comprises data fitting the plurality of first phase difference measurements to a mathematical expression that corresponds to a phase difference generated by one of the zeroth order concomitant gradient field, first order concomitant gradient field or second order concomitant gradient field.

10. The method of claim 1, wherein a zeroth order component of the concomitant gradient field is corrected by adjusting a frequency of an MRI system receiver and transmitter.

11. The method of claim 1, wherein the compensatory gradient waveforms are pre-calculated in an MRI pulse sequence memory or are calculated in real-time in a pre-emphasis board.

12. A method for correcting concomitant gradient field effects in a magnetic resonance imaging (MRI) system, the method comprising:
   determining a plurality of first phase difference measurements between two acquisitions using a plurality of first bipolar gradient waveforms applied to a first gradient coil;
   determining a plurality of second phase difference measurements between two acquisitions using a plurality of second bipolar gradient waveforms applied to a second gradient coil;
   determining first and second gradient coil constants based on the plurality of first phase difference measurements and the plurality of second phase difference measurements respectively;
   determining compensatory gradient waveforms based on the first and second gradient coil constants; and
   applying the compensatory gradient waveforms with target gradient waveforms to compensate for a concomitant gradient field.

13. The method of claim 1, wherein the first and second bipolar gradient waveforms each include two gradient lobes of positive and negative polarities.

14. The method of claim 13, wherein at least one of the first bipolar gradient waveforms in each acquisition is reduced to a single gradient lobe depending on whether the gradient coils are in a readout direction or a phase encoding direction.

15. The method of claim 14, wherein the gradient lobe of the plurality of first bipolar gradient waveforms which are not reduced to the single gradient lobe are varied in a step fashion such that the phase difference is less than $2\pi$.

16. The method of claim 12, wherein determining the first and second gradient coil constants comprise data fitting the plurality of first and second phase difference measurements to mathematical expressions that correspond to a phase difference generated by one of the zeroth order concomitant gradient field, first order concomitant gradient field or second order concomitant gradient field.

17. The method of claim 12, wherein a zeroth order component of the concomitant gradient field is corrected by adjusting a frequency of an MRI system receiver and transmitter.

18. The method of claim 12, wherein the compensatory gradient waveforms are pre-calculated in an MRI pulse sequence memory or are calculated in real-time in a pre-emphasis board.

19. A magnetic resonance imaging (MRI) system, comprising:
   a magnet configured to generate a polarizing magnetic field about at least a portion of a subject arranged in the MRI system;
   a gradient coil assembly including a plurality of gradient coils configured to apply at least one gradient field to the polarizing magnetic field;
   a radio frequency (RF) system configured to apply an RF field to the subject and to receive magnetic resonance signals from the subject;
   a processing system programmed to:
      determine a plurality of phase difference measurements between two acquisitions using a plurality of bipolar gradient waveforms applied to at least one gradient coil of the plurality of gradient coils;
      determine at least one gradient coil constant based on the plurality of phase difference measurements;
      determine compensatory gradient waveforms based on the at least one gradient coil constant; and
      apply the compensatory gradient waveforms to the plurality of gradient coils to compensate for a concomitant gradient field.

20. The MRI system of claim 19, wherein the processing system is programmed to determine compensatory gradient waveforms based on the at least one gradient coil constant so as to generate a concomitant correction gradient field in the same direction as the concomitant gradient field.

* * * * *